United States Patent
Weir et al.

(10) Patent No.: US 10,478,170 B2
(45) Date of Patent: *Nov. 19, 2019

(54) T-FASTENER SUTURE DELIVERY SYSTEM

(71) Applicant: C. R. Bard, Inc., Murray Hill, NJ (US)

(72) Inventors: Steven A. Weir, Sandy, UT (US);
Glade H. Howell, Draper, UT (US);
Michael Barenboym, Cambridge, MA (US); Kenneth A. Eliasen, Wrentham, MA (US); Matthew J. Cohn, Cranston, RI (US)

(73) Assignee: C. R. Bard, Inc., Murray Hill, NJ (US)

( * ) Notice: Subject to any disclaimer, the term of this patent is extended or adjusted under 35 U.S.C. 154(b) by 338 days.

This patent is subject to a terminal disclaimer.

(21) Appl. No.: 15/453,783

(22) Filed: Mar. 8, 2017

(65) Prior Publication Data

US 2017/0172563 A1    Jun. 22, 2017

Related U.S. Application Data

(63) Continuation of application No. 13/370,100, filed on Feb. 9, 2012, now Pat. No. 9,592,044.

(Continued)

(51) Int. Cl.
*A61B 17/04* (2006.01)
*A61B 17/00* (2006.01)

(52) U.S. Cl.
CPC ...... *A61B 17/0401* (2013.01); *A61B 17/0482* (2013.01); *A61B 17/0487* (2013.01);
(Continued)

(58) Field of Classification Search
CPC ............ A61B 17/0401; A61B 17/0482; A61B 17/0487; A61B 2017/0409;
(Continued)

(56) References Cited

U.S. PATENT DOCUMENTS 3,443,725 A    5/1969   Lawhorn
4,705,040 A   11/1987   Mueller et al.
(Continued)

FOREIGN PATENT DOCUMENTS

WO   2004105620 A1   12/2004
WO   2009011824 A1    1/2009
(Continued)

OTHER PUBLICATIONS

Boston Scientific Easy Tie brochure, 2009.
(Continued)

*Primary Examiner* — Kathleen S Holwerda
(74) *Attorney, Agent, or Firm* — Rutan & Tucker LLP

(57) ABSTRACT

A delivery device for inserting a plurality of T-fastener-equipped sutures into a body of a patient in a spaced-apart configuration for the purpose of securing the stomach wall against the abdominal wall, also known as gastropexy, is disclosed. The suture delivery device is configured to deliver multiple sutures using a single needle and without need for reloading, saving time and effort for the clinician and simplifying the suture placement process. In one embodiment, a T-fastener-equipped suture delivery device comprises a housing, a hollow needle extending from the housing, and a plurality of T-fastener-equipped sutures at least partially disposed within one of the needle and the housing. An ejection assembly for successively ejecting the T-fasteners from a distal end of the needle without reloading the delivery device is also included in the housing.

13 Claims, 20 Drawing Sheets

Related U.S. Application Data

(60) Provisional application No. 61/441,105, filed on Feb. 9, 2011.

(52) U.S. Cl.
CPC ........... A61B 2017/00477 (2013.01); A61B 2017/00818 (2013.01); A61B 2017/0409 (2013.01); A61B 2017/0417 (2013.01); A61B 2017/0488 (2013.01)

(58) Field of Classification Search
CPC .... A61B 2017/0417; A61B 2017/0488; A61B 17/062; A61B 17/06109; A61B 17/0469
See application file for complete search history.

(56) References Cited

U.S. PATENT DOCUMENTS

| | | | |
|---|---|---|---|
| 4,741,330 A | 5/1988 | Hayhurst | |
| 5,041,129 A | 8/1991 | Hayhurst et al. | |
| 5,074,846 A | 12/1991 | Clegg et al. | |
| 5,123,914 A | 6/1992 | Cope | |
| RE34,021 E | 8/1992 | Mueller et al. | |
| 5,167,627 A | 12/1992 | Clegg et al. | |
| 5,307,924 A | 5/1994 | Manosalva et al. | |
| 5,318,534 A | 6/1994 | Williams et al. | |
| 5,341,823 A | 8/1994 | Manosalva et al. | |
| 5,458,583 A | 10/1995 | McNeely et al. | |
| 5,507,754 A * | 4/1996 | Green ............... A61B 17/0401 112/169 |
| 5,520,696 A | 5/1996 | Wenstrom, Jr. | |
| 5,531,678 A | 7/1996 | Tomba et al. | |
| 5,531,699 A | 7/1996 | Tomba et al. | |
| 5,531,759 A | 7/1996 | Kensey et al. | |
| 5,545,178 A | 8/1996 | Kensey et al. | |
| 5,547,458 A | 8/1996 | Ortiz et al. | |
| 5,573,542 A | 11/1996 | Stevens | |
| 5,601,571 A | 2/1997 | Moss | |
| 5,613,939 A | 3/1997 | Failla | |
| 5,626,614 A | 5/1997 | Hart | |
| 5,647,874 A | 7/1997 | Hayhurst | |
| 5,702,352 A | 12/1997 | Kimura et al. | |
| 5,741,278 A | 4/1998 | Stevens | |
| 5,948,000 A | 9/1999 | Larsen et al. | |
| 5,948,001 A | 9/1999 | Larsen | |
| 5,951,576 A | 9/1999 | Wakabayashi | |
| 5,972,024 A | 10/1999 | Northrup, III et al. | |
| 6,030,402 A | 2/2000 | Thompson et al. | |
| 6,066,146 A | 5/2000 | Carroll et al. | |
| 6,110,183 A | 8/2000 | Cope | |
| 6,315,789 B1 | 11/2001 | Cragg | |
| 6,425,900 B1 | 7/2002 | Knodel et al. | |
| 6,488,691 B1 | 12/2002 | Carroll et al. | |
| 6,494,888 B1 | 12/2002 | Laufer et al. | |
| 6,500,184 B1 | 12/2002 | Chan et al. | |
| 6,506,196 B1 | 1/2003 | Laufer | |
| 6,551,333 B2 | 4/2003 | Kuhns et al. | |
| 6,656,182 B1 | 12/2003 | Hayhurst | |
| 6,663,639 B1 | 12/2003 | Laufer et al. | |
| 6,699,263 B2 | 3/2004 | Cope | |
| 6,736,828 B1 | 5/2004 | Adams et al. | |
| 6,821,285 B2 | 11/2004 | Laufer et al. | |
| 6,981,983 B1 | 1/2006 | Rosenblatt et al. | |
| 6,997,932 B2 | 2/2006 | Dreyfuss et al. | |
| 7,041,111 B2 | 5/2006 | Chu | |
| 7,056,325 B1 | 6/2006 | Makower et al. | |
| 7,066,944 B2 | 6/2006 | Laufer et al. | |
| 7,074,229 B2 | 7/2006 | Adams et al. | |
| 7,083,595 B2 | 8/2006 | Chu et al. | |
| 7,083,630 B2 | 8/2006 | DeVries et al. | |
| 7,341,558 B2 | 3/2008 | de la Torre et al. | |
| 7,390,329 B2 | 6/2008 | Westra et al. | |
| 7,485,124 B2 | 2/2009 | Kuhns et al. | |
| 7,494,496 B2 | 2/2009 | Swain et al. | |
| 7,645,286 B2 | 1/2010 | Catanese, III et al. | |
| 7,670,279 B2 | 3/2010 | Gertner | |
| 7,736,378 B2 | 6/2010 | Maahs et al. | |
| 7,758,594 B2 | 7/2010 | Lamson et al. | |
| 7,771,438 B2 | 8/2010 | Dreyfuss et al. | |
| 7,776,057 B2 | 8/2010 | Laufer et al. | |
| 7,815,655 B2 | 10/2010 | Catanese, III et al. | |
| 7,815,662 B2 | 10/2010 | Spivey et al. | |
| 7,833,235 B2 | 11/2010 | Chu | |
| 7,837,698 B2 | 11/2010 | DeVries et al. | |
| 7,850,607 B2 | 12/2010 | de la Torre et al. | |
| 7,881,797 B2 | 2/2011 | Griffin et al. | |
| 7,905,893 B2 | 3/2011 | Kuhns | |
| 7,935,128 B2 | 5/2011 | Rioux et al. | |
| 8,029,462 B2 | 10/2011 | Chu et al. | |
| 8,043,261 B2 | 10/2011 | Weststrate et al. | |
| 8,070,743 B2 | 12/2011 | Kagan et al. | |
| RE43,143 E | 1/2012 | Hayhurst | |
| 8,157,816 B2 | 4/2012 | Rotella et al. | |
| 9,592,044 B2 * | 3/2017 | Weir ................. A61B 17/0401 |
| 2003/0191497 A1 | 10/2003 | Cope | |
| 2005/0154401 A1 | 7/2005 | Weldon et al. | |
| 2005/0251159 A1 | 11/2005 | Ewers et al. | |
| 2005/0271617 A1 | 12/2005 | Shirahama et al. | |
| 2006/0020247 A1 | 1/2006 | Kagan et al. | |
| 2006/0100643 A1 | 5/2006 | Laufer et al. | |
| 2006/0235446 A1 | 10/2006 | Godin | |
| 2006/0241661 A1 | 10/2006 | DeVries et al. | |
| 2007/0100376 A1 | 5/2007 | Mikkaichi et al. | |
| 2007/0156117 A1 | 7/2007 | Adams et al. | |
| 2007/0233005 A1 | 10/2007 | McMichael et al. | |
| 2007/0270889 A1 | 11/2007 | Conlon et al. | |
| 2007/0276408 A1 | 11/2007 | Filipi et al. | |
| 2008/0058887 A1 | 3/2008 | Griffin et al. | |
| 2008/0103441 A1 | 5/2008 | Melsheimer | |
| 2008/0269781 A1 | 10/2008 | Funamura et al. | |
| 2009/0062742 A1 | 3/2009 | Rotella et al. | |
| 2009/0062743 A1 | 3/2009 | Rotella et al. | |
| 2009/0198256 A1 | 8/2009 | Funamura | |
| 2009/0326561 A1 | 12/2009 | Carroll, II et al. | |
| 2010/0023025 A1 | 1/2010 | Zeiner et al. | |
| 2010/0023026 A1 | 1/2010 | Zeiner et al. | |
| 2010/0094212 A1 | 4/2010 | Weststrate et al. | |
| 2010/0268256 A1 | 10/2010 | Dreyfuss et al. | |
| 2011/0028999 A1 | 2/2011 | Chu | |
| 2011/0124963 A1 | 5/2011 | DeVries et al. | |
| 2011/0125211 A1 | 5/2011 | Griffin et al. | |
| 2011/0202074 A1 | 8/2011 | Talmo et al. | |
| 2011/0288488 A1 | 11/2011 | Melsheimer | |
| 2012/0010570 A1 | 1/2012 | Weststrate et al. | |
| 2012/0203250 A1 | 8/2012 | Weir et al. | |

FOREIGN PATENT DOCUMENTS

| | | |
|---|---|---|
| WO | 2009027883 A2 | 3/2009 |
| WO | 2009143331 A1 | 11/2009 |
| WO | 2010009184 A1 | 1/2010 |
| WO | 2010011826 A2 | 1/2010 |
| WO | 2012109455 A1 | 8/2012 |

OTHER PUBLICATIONS

Kimberley-Clark MIC G Introducer Kit Instructions for Use, date unknown.
PCT/US12/24499 International Preliminary Report on Patentability dated Aug. 13, 2013.
PCT/US12/24499 International Search Report and Written Opinion dated Jun. 29, 2012.
U.S. Appl. No. 13/370,100, filed Feb. 9, 2012 Final Office Action dated Apr. 14, 2015.
U.S. Appl. No. 13/370,100, filed Feb. 9, 2012 Final Office Action dated Dec. 24, 2015.
U.S. Appl. No. 13/370,100, filed Feb. 9, 2012 Non-Final Office Action dated Aug. 26, 2015.

(56) References Cited

OTHER PUBLICATIONS

U.S. Appl. No. 13/370,100, filed Feb. 9, 2012 Non-Final Office Action dated Dec. 4, 2014.

* cited by examiner

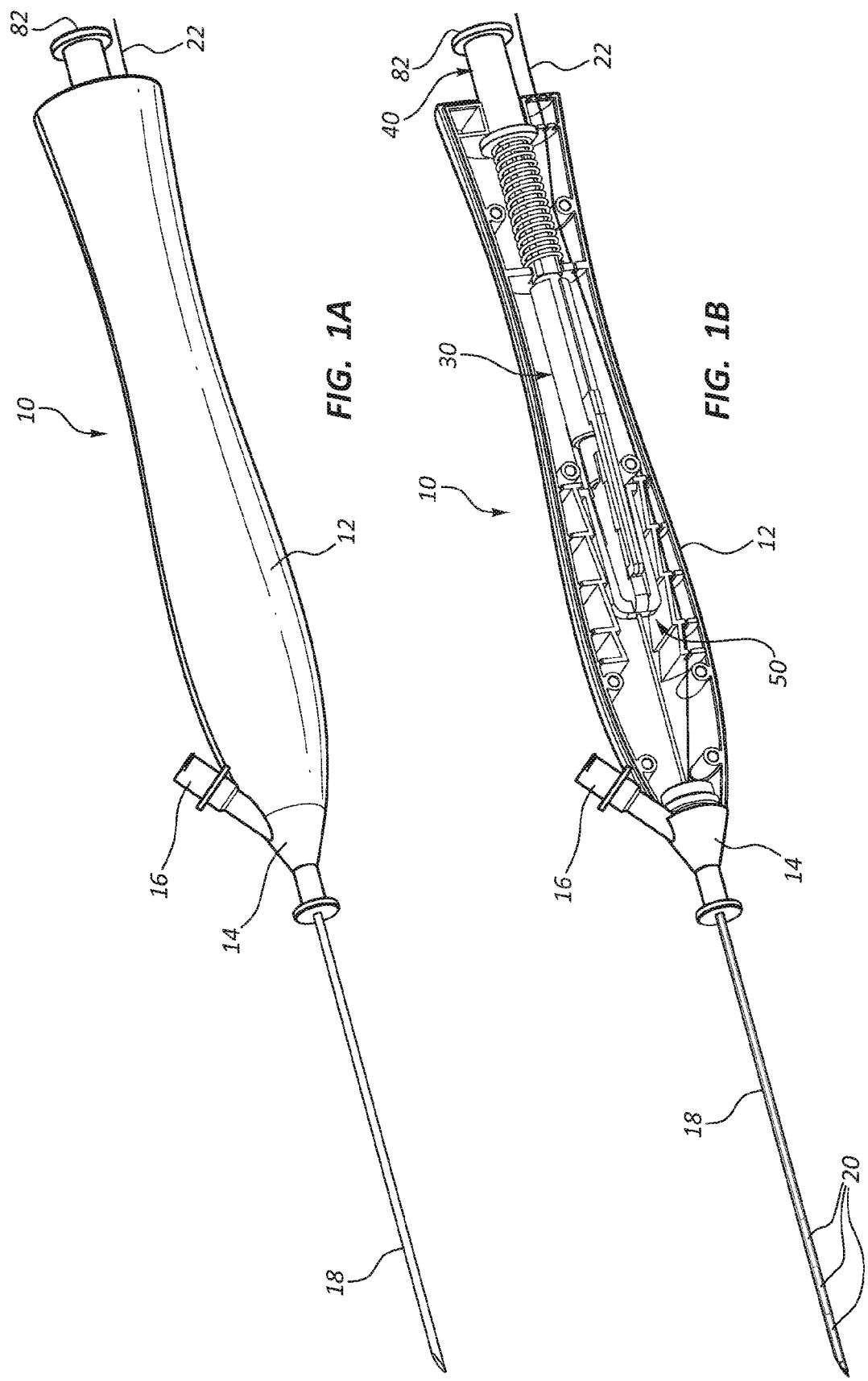

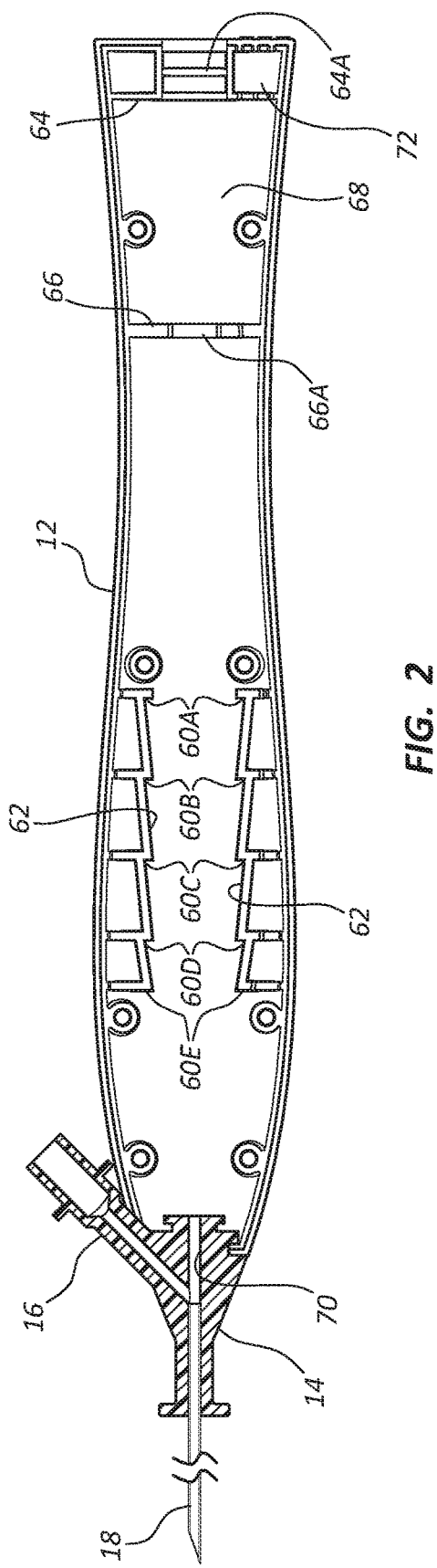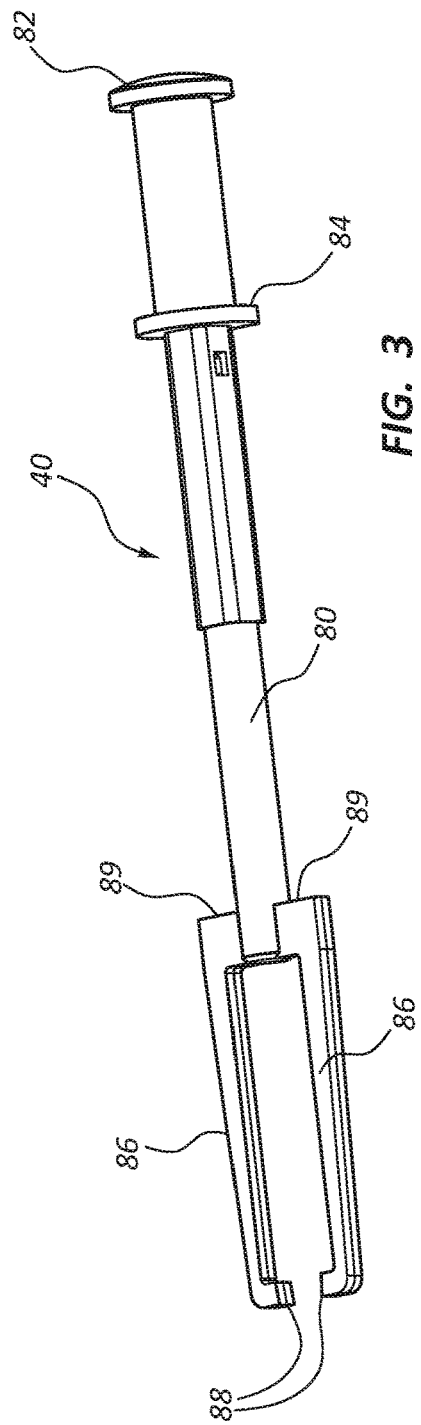
FIG. 2
FIG. 3

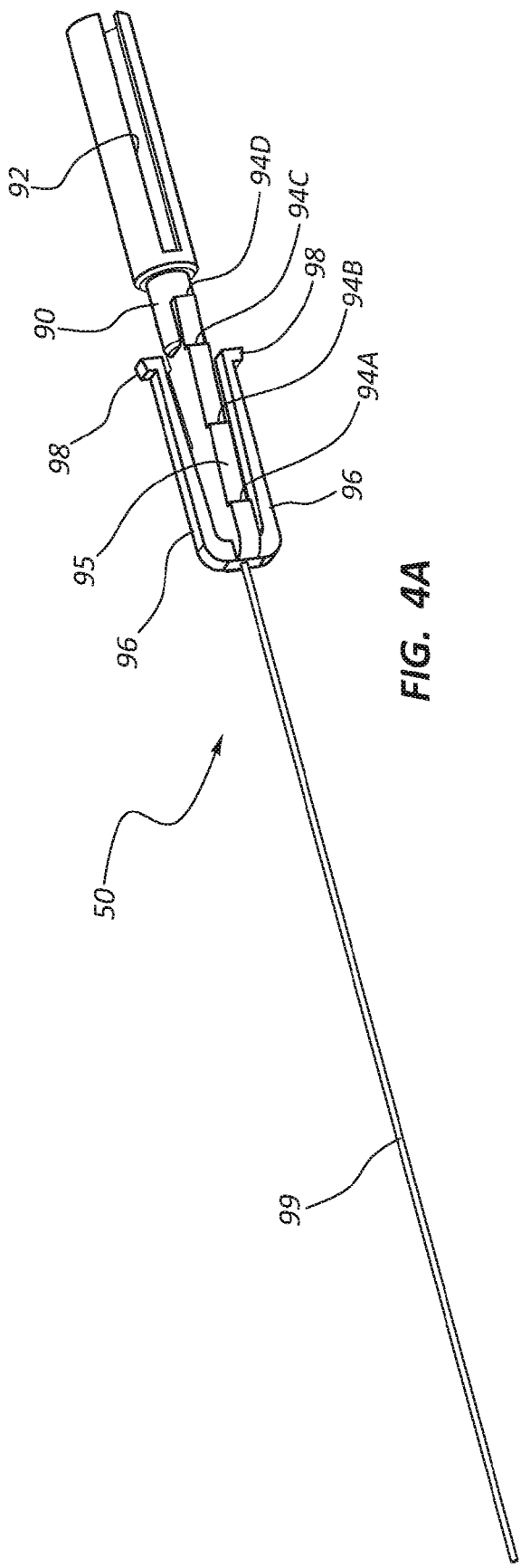
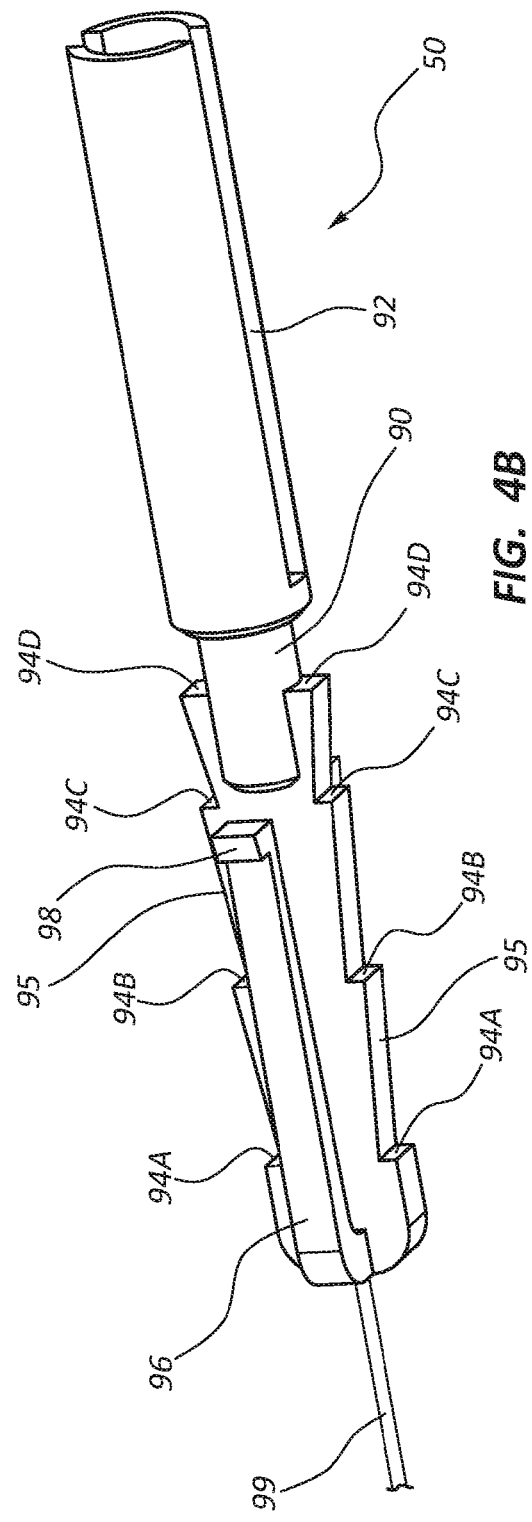
FIG. 4A
FIG. 4B

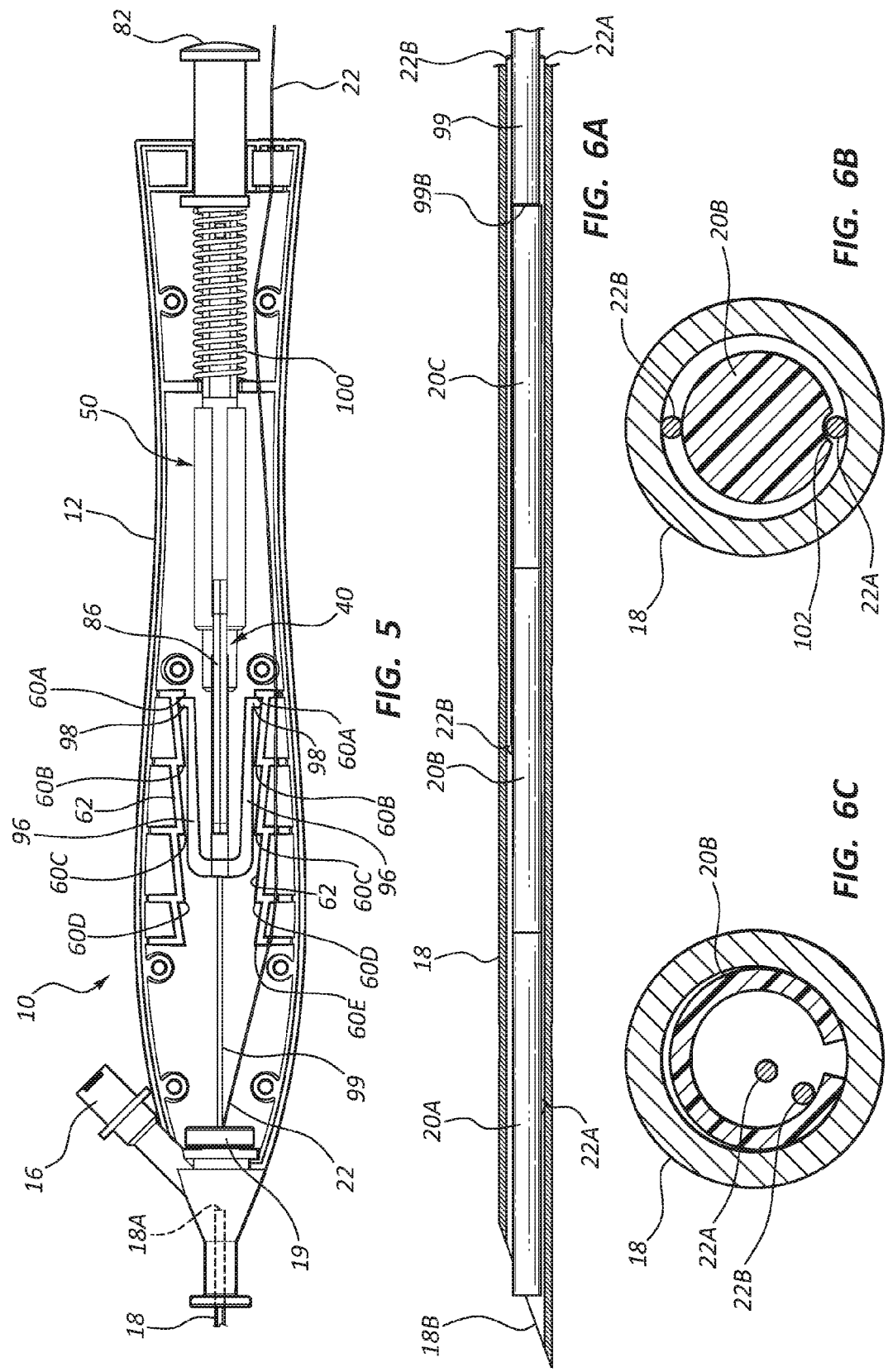

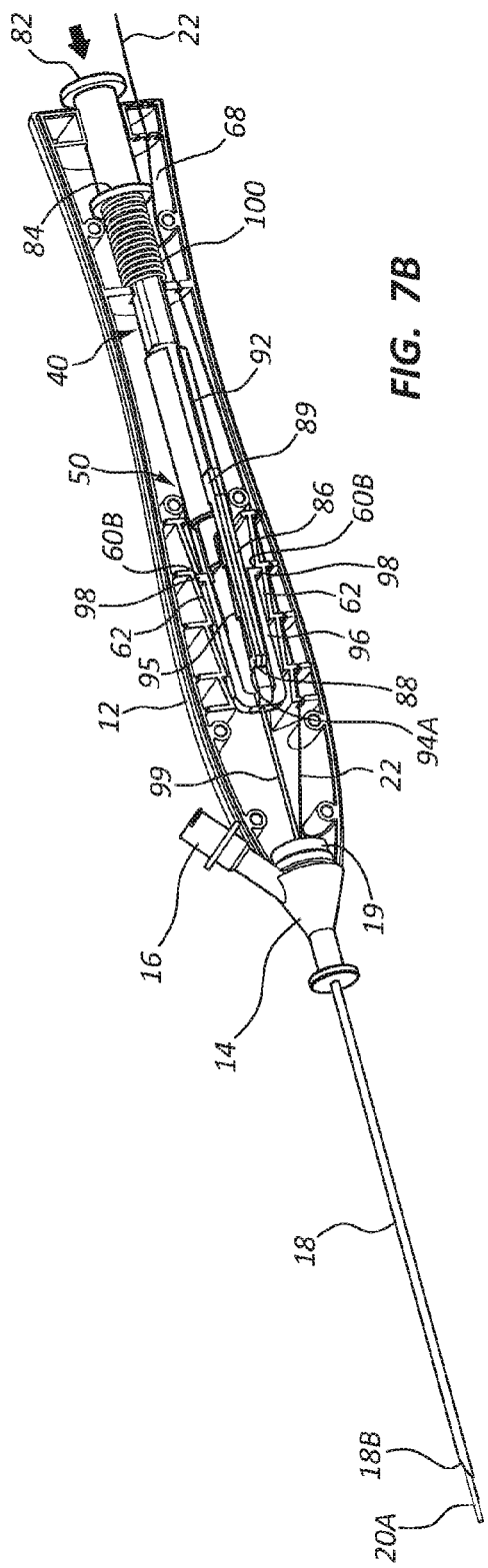
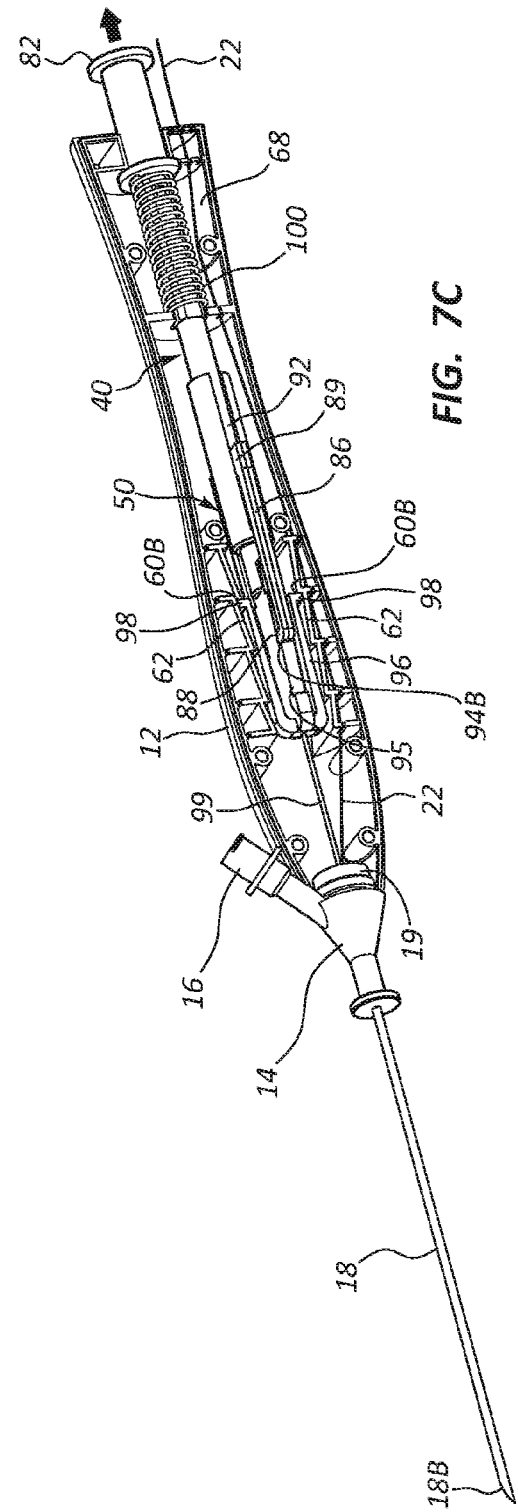
FIG. 7B
FIG. 7C

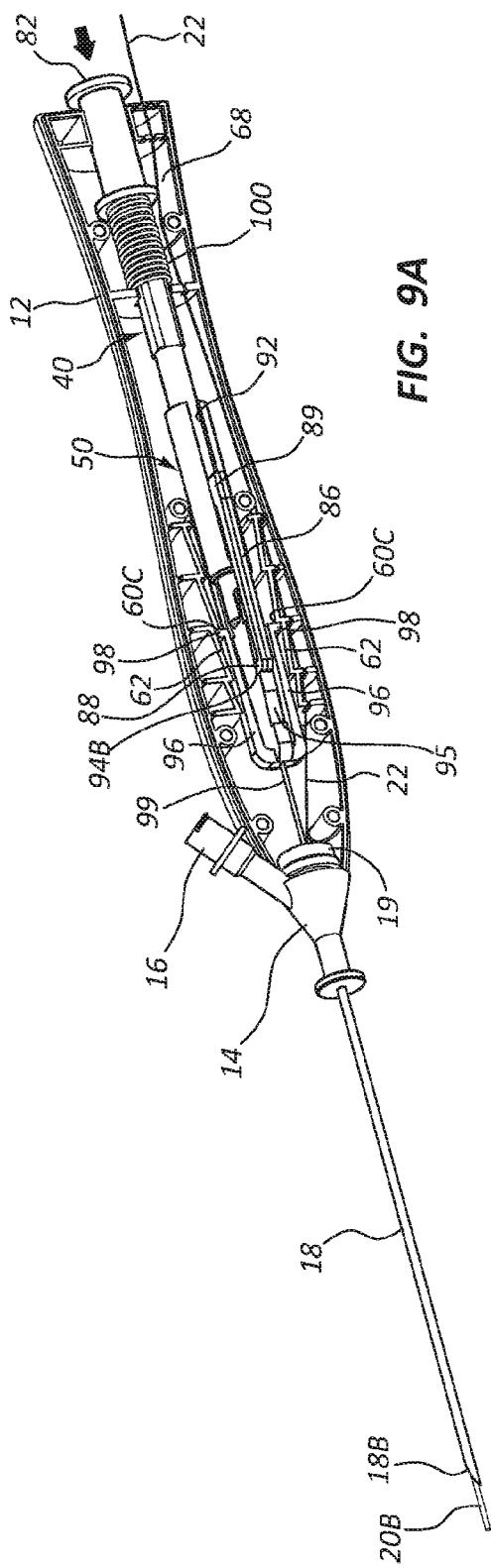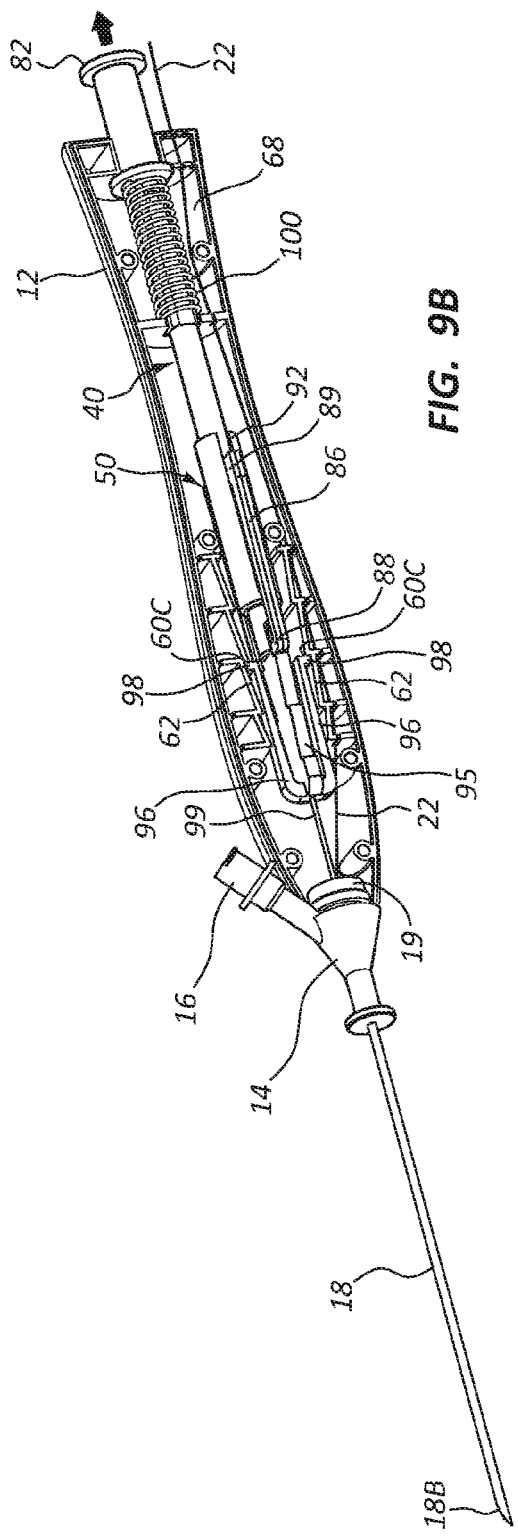

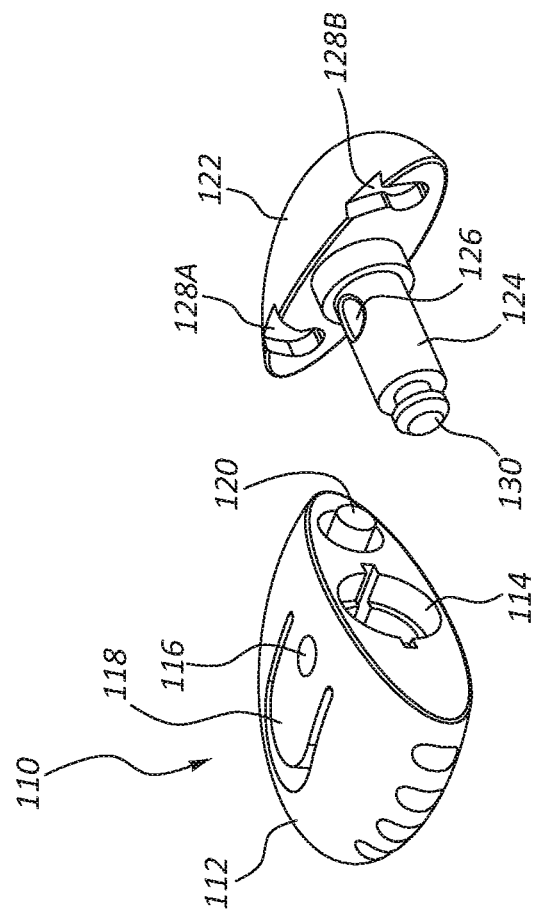
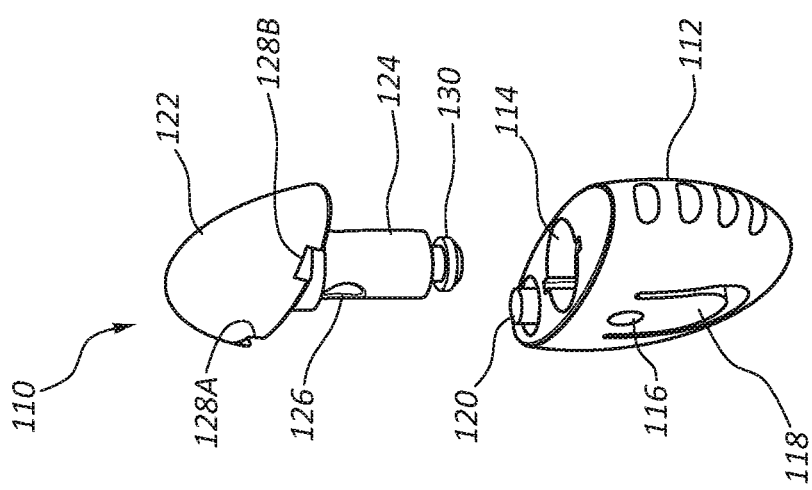
FIG. 13B
FIG. 13A

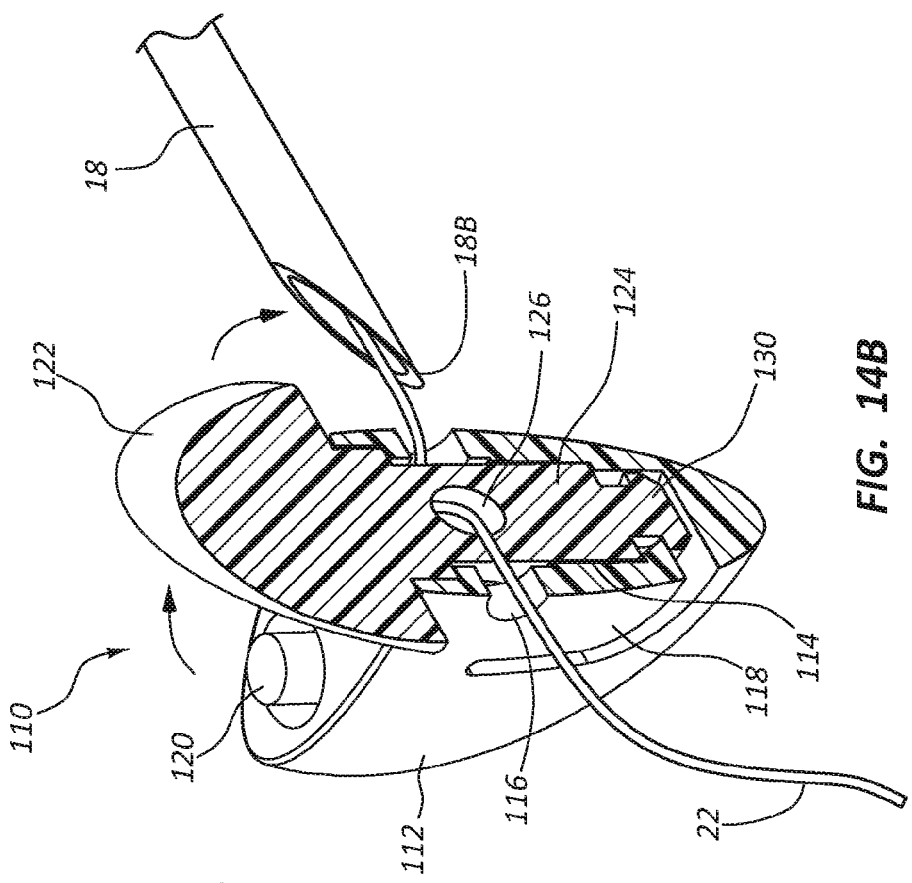
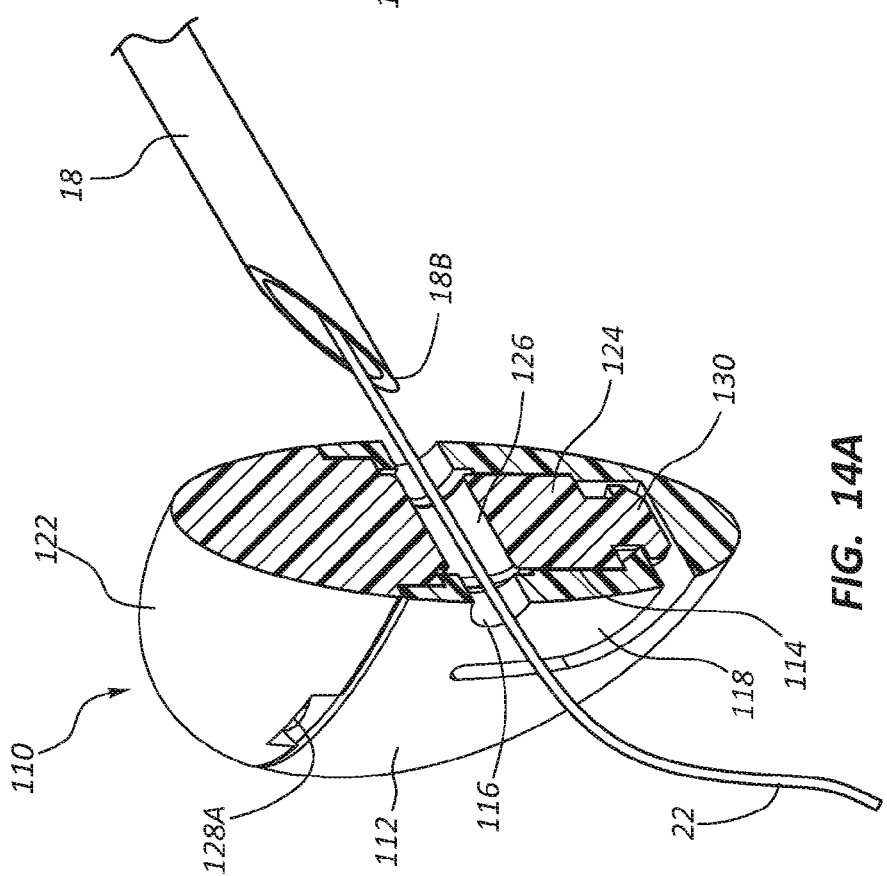

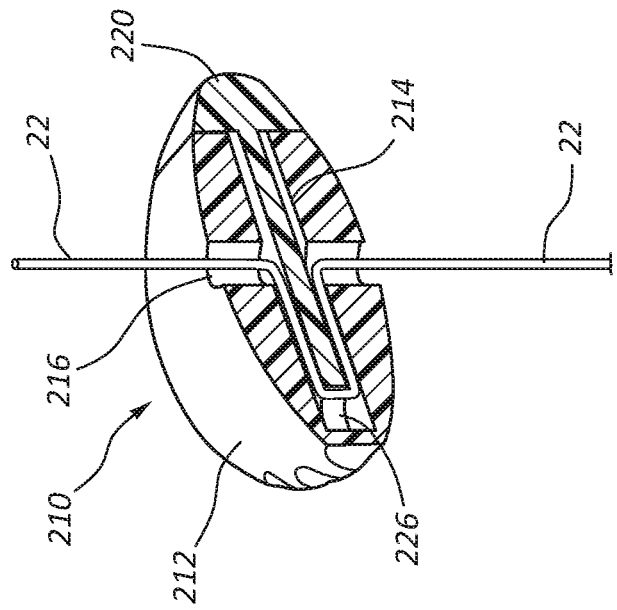
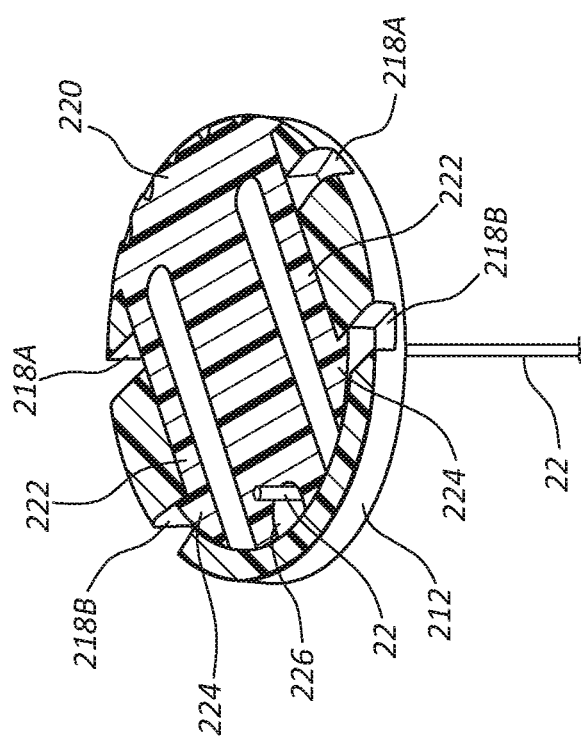
FIG. 16D
FIG. 16C

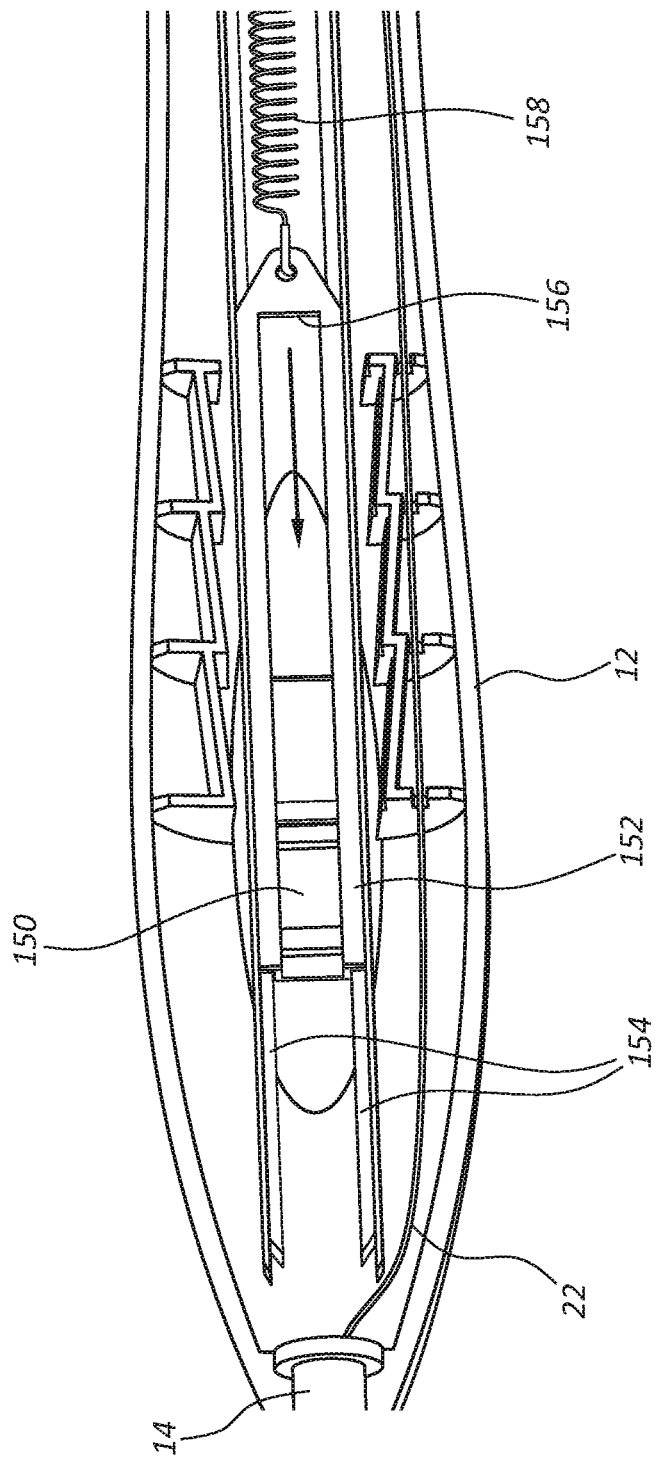

US 10,478,170 B2

T-FASTENER SUTURE DELIVERY SYSTEM

CROSS-REFERENCE TO RELATED APPLICATIONS

This application is a continuation of U.S. patent application Ser. No. 13/370,100, filed Feb. 9, 2012, now U.S. Pat. No. 9,592,044, which claims the benefit of U.S. Provisional Patent Application No. 61/441,105, filed Feb. 9, 2011, and titled "T-Fastener-Equipped Suture Delivery System for Gastropexy," each of which is incorporated herein by reference in its entirety.

BRIEF SUMMARY

Briefly summarized, embodiments of the present invention are directed to a delivery device and associated methods for inserting a plurality of T-fastener-equipped sutures into a body of a patient in a spaced-apart configuration for the purpose of securing the stomach wall against the abdominal wall, also known as gastropexy. The suture delivery device is configured to deliver multiple sutures using a single needle and without need for reloading, saving time and effort for the clinician and simplifying the suture placement process.

In one embodiment, a T-fastener-equipped suture delivery device comprises a housing, a hollow needle extending from the housing, and a plurality of T-fastener-equipped sutures at least partially disposed within one of the needle and the housing. An ejection assembly for successively ejecting the T-fasteners from a distal end of the needle without reloading the delivery device is also included in the housing.

In one embodiment, three T-fastener-equipped sutures can be pre-loaded in and deployed by the delivery device in a triangle arrangement so as to secure the stomach wall of the patient against the abdominal wall. An enteral feeding tube or other feeding device can then be percutaneously inserted in the region between the three placed T-fastener-equipped sutures before the sutures are then removed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 1A-1C are various views of a T-fastener-equipped suture delivery device in accordance with one embodiment;

FIG. 2 is a cross sectional view of the housing of the T-fastener suture delivery device of FIGS. 1A-1C;

FIG. 3 is a perspective view of an actuator of the T-fastener suture delivery device of FIGS. 1A-1C;

FIGS. 4A and 4B are various views of an ejector of the T-fastener suture delivery device of FIGS. 1A-1C;

FIG. 5 is a cross-sectional side view of the T-fastener suture delivery device of FIGS. 1A-1C;

FIGS. 6A and 6B are various views showing disposal of T-fasteners in a needle of a T-fastener suture delivery device according to one embodiment;

FIG. 6C is a cross-sectional view showing disposal of a T-fastener in the needle of a T-fastener suture delivery device according to one embodiment;

FIGS. 7A-7C are various cross-sectional views of the T-fastener suture delivery device of FIGS. 1A-1C, showing operation thereof according to one embodiment;

FIGS. 9A and 9B are various cross-sectional views of the T-fastener suture delivery device of FIGS. 1A-1C, showing operation thereof according to one embodiment;

FIGS. 13A and 13B are perspective views of an external bolster according to one embodiment;

FIGS. 14A and 14B are cross sectional views showing actuation of the external bolster of FIGS. 13A and 13B in capturing a suture;

FIGS. 16A-16D are various views showing actuation of the external bolster of FIGS. 15A and 15B, in capturing a suture;

FIGS. 18A and 18B are various cross-sectional views of the T-fastener suture delivery device of FIG. 17.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle placed within the body of a patient is considered a distal end of the needle, while the needle end remaining outside the body is a proximal end of the needle. Also, the words "including," "has," and "having," as used herein, including the claims, shall have the same meaning as the word "comprising."

Embodiments of the present invention are generally directed to a delivery system for inserting a plurality of T-fastener-equipped sutures into a body of a patient in a spaced-apart configuration for the purpose of securing the stomach wall against the abdominal wall, also known as gastropexy. This in turn enables an enteral feeding tube to be percutaneously inserted into the stomach in the region where the T-fastener-equipped sutures were placed. For instance, three T-fastener sutures are typically placed in a triangle arrangement so as to secure the stomach wall of the patient against the abdominal wall. A feeding device is then percutaneously inserted in the region between the three placed T-fastener sutures.

The suture delivery device disclosed herein is configured to deliver multiple sutures using a single needle and without need for reloading, saving time and effort for the clinician and simplifying the suture placement process.

Figure 1C:
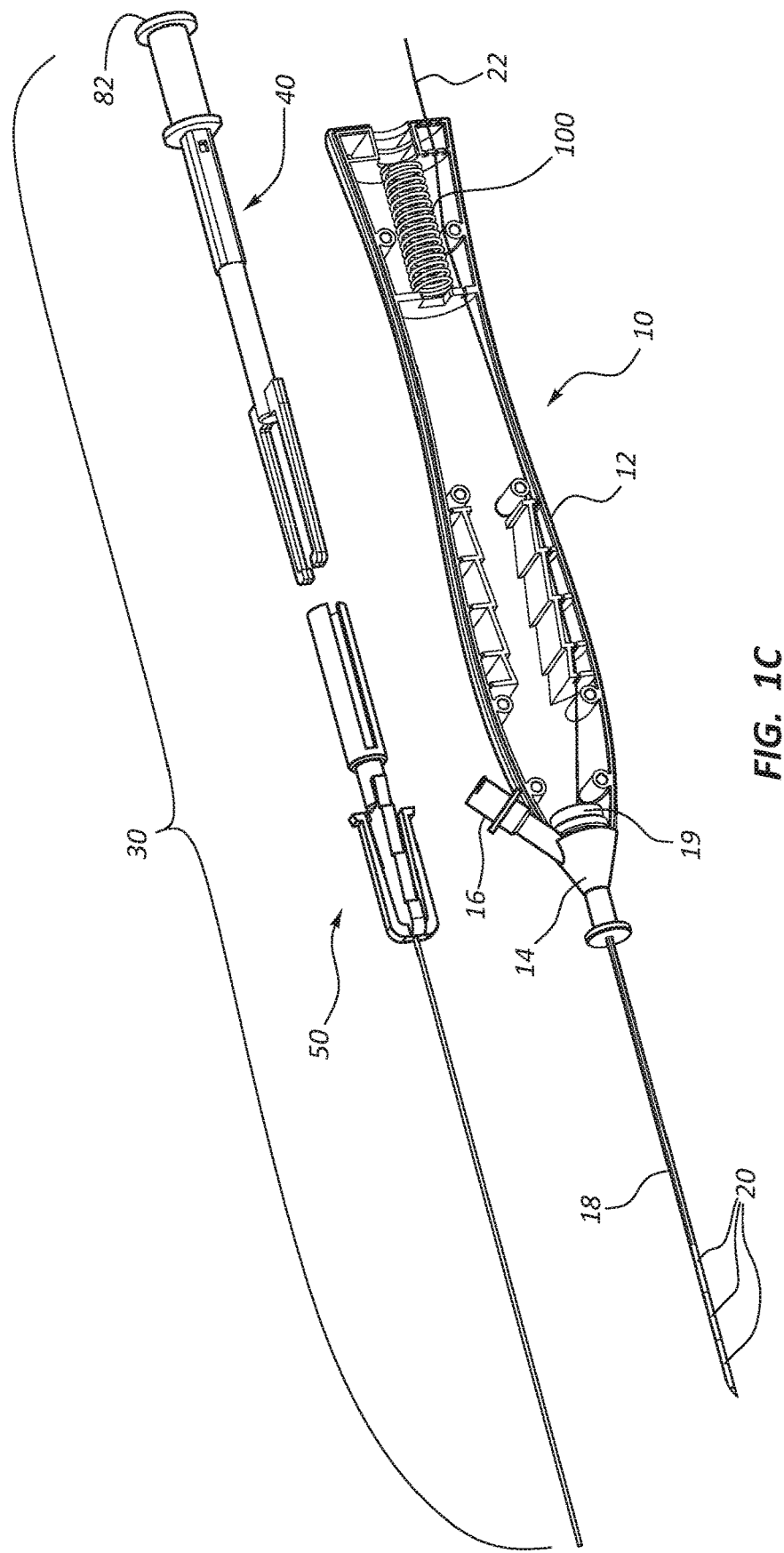

Reference is first made to FIGS. 1A-1C, which show various details regarding a T-fastener suture delivery device ("device"), generally designated at 10, for use in a gastropexy or other suitable procedure, according to one embodiment. The device 10 is designed to dispense one, two, three, or more T-fastener-equipped sutures without reloading. Further, and as will be seen below, the device 10 can be included as part of a system, providing an external bolster for securing each T-fastener suture after placement into the patient's body, all in a single device.

As shown, in the present embodiment the device 10 includes a housing 12 in which select device components are housed. The housing 12 is shaped in the present embodiment so as to facilitate handheld use. A hub 14, from which distally extends a hollow needle 16, is disposed at the distal end of the housing 12. An injection port 16 is included with the hub 14 to enable a clinician, for instance, to check for the presence of gastric fluids in the needle 18 to ensure adequate insertion of the needle into the patient. In one instance, a fluid-filled syringe can be attached to the injection port 16 and the plunger retracted to check for the presence of bubbles entering into the syringe, which confirms the placement of the distal tip 18B of the needle 18 within the stomach cavity. The conduit provided by the hollow needle 18 extends through the hub 14 into the interior of the housing 12. In one embodiment, a valve 19, such as a silicone slit valve, is disposed at the proximal end of the hub 14 so as to prevent gastric fluids from travelling from the needle 18 into the interior of the housing 12. FIG. 1A further shows an actuation button 82 disposed at a proximal end of the housing 12 and a suture 22 extending from the housing. These components are discussed further below.

As best seen in FIGS. 1B and 1C, the device 10 further includes a plurality of T-fasteners 20 pre-disposed in the needle 18. In the present embodiment, three T-fasteners 20A, 20B, and 20C (see also FIG. 6A) are disposed in the needle 18, though it is appreciated that other numbers of T-fasteners can be used. The T-fasteners 20 are linearly placed end-to-end within the conduit of the needle 18, and each T-fastener has attached thereto a corresponding wire suture 22A, 22B, or 22C, respectively. The sutures 22A-22C extend proximally up the conduit of the needle 18, into the interior of the housing 12, and out a hole defined in the housing, depending on the lengths thereof In another embodiment, one or more of the sutures can extend out through a hole defined in the needle so as to provide more room in the conduit of the needle. Each T-fastener 20 is configured to extend in a perpendicular configuration with respect to a proximate portion of its corresponding suture 22, though when constrained within the needle 18 each T-fastener and its suture are substantially parallel to one another. In one embodiment, the sutures 22A-22C can include silk, nylon, polypropylene, and can further include absorbable materials such as polylactic acid, polydioxanone, and the like.

FIGS. 1A-1C further depict details of an ejection assembly 30 for use in selectively ejecting each T-fastener 20, together with its corresponding suture 22, from the distal end of the needle for insertion into the body of a patient, for instance. As shown, the ejection assembly 30 generally includes an actuator 40 and an ejector 50. A main spring 100 is included to enable iterative, back-and-forth linear movement of the actuator 40 with respect to the ejector 50, as will be described further below.

FIG. 2 illustrates various features included with the housing 12 to enable operation of the ejection assembly 30. As shown, a plurality of pairs of pockets 60A-60E are defined by two opposing sets of proximally inclined teeth 62A-62D. The pockets 60A-60E and the inclined teeth 62A-62D provide for one-way, step-wise distal movement of the ejector 50 when iteratively advanced by the actuator 40, as will be shown. A proximal spring surface 64 defining a hole 64A and a distal spring surface 66 defining a hole 66A bound a spring cavity 68 wherein is disposed the main spring 100 (FIGS. 1B, 1C). The holes 64A and 66A enable the body of the actuator 40 to extend through the spring cavity 68. FIG. 2 further shows that the hub 14 defines a conduit 70 in which a proximal portion of the needle 18 is disposed so as to provide communication of the needle conduit with the interior of the housing 12. Note that the housing can be manufactured any number of suitable ways so as to include the features described here, including injection molding, casting, machining, etc. Further, the housing 12 and ejection assembly 30 can include metal, plastic, or other suitable materials. Also note that the T-fastener can be manufactured from any suitable materials(s) including plastic, metal, bioabsorbable materials, etc.

FIG. 3 depicts various details of the actuator 40 according to the present embodiment, which is employed to provide one-way, step-wise distal movement of the ejector 50 when manually actuated by a user. In particular, the actuator 40 includes an elongate body 80 that defines an actuation button 82 on its proximal end. An annular flange 84 is included distal to the button 82 to prevent separation of the actuator 40 from the housing 12 (see also FIG. 1C).

A pair of actuator arms 86 extend distally from the actuator body 40 in a parallel fashion. A shoulder 89 is defined by a proximal portion of each arm 86. Each arm 86 further defines at its distal end an inwardly extending foot 88, the feet pointing toward one another in a spaced-apart configuration. As will be seen, the arms 86 and feet 88 engage features of the ejector 50 to enable its incremental, one-way distal movement. Note that, though manually activated here, in other embodiments the actuator could be automatically, electrically, or electronically actuated by a motor or other non-manual configuration.

FIGS. 4A and 4B depict various details of the ejector 50 according to the present embodiment. As mentioned, the ejector 50 is configured to distally move in a linear one-way fashion in order to selectively eject the T-fasteners 20 from the needle in the manner to be described further below. The ejector 50 in the present embodiment includes an elongate body 90, a proximal portion of which defines a slot 92 for receipt of the arms 86 of the actuator therein. Two sets of pockets 94A-94D are defined by two corresponding sets of distally inclined teeth 95 that are defined on opposing sides of the ejector body, as best seen in FIG. 4B.

FIG. 4A shows that the ejector 50 further includes two ejector arms 96 that originate at a distal portion of the ejector body 90 and extend in a proximal direction parallel to one another. Each arm 96 further defines at its terminal end an outwardly extending foot 98. As will be seen, the arms 96 and feet 98 of the ejector engage the pockets 60A-60E of the housing 12 to ensure one-way distal movement of the ejector. A push rod 99 extends distally from the ejector body 90 and is configured to be received into the conduit of the needle 18, as seen in FIG. 1B, to enable selective ejection of one or more of the T-fasteners 20 disposed within the needle. The length of the push rod 99 corresponds in one embodiment to the overall size of the device 10 and the number of T-fasteners 20 that are to be deployed by the device. Thus, the size of this and the other components described herein can vary according to need, application, etc. The push rod 99 here is solid, though in other embodiments it could be hollow to enable the sutures to pass therethrough.

FIG. 5 shows the interengagement of the actuator 40 with the ejector 50, wherein the actuator arms 86 are received into the ejector slot 92 such that the actuator arm shoulders 89 are disposed proximate the distal end of the slot. The ejector arms 96 are positioned such that the feet 98 thereof engage the pockets 60A of the housing 12. This engagement prevents proximal movement of the ejector 50, but enables distal movement thereof by virtue of the design of the inclined teeth 62.

The push rod 99 of the ejector 50 is shown penetrating the conduit 70 of the hub 14 and extends into the conduit of the needle 18. As seen in FIG. 6A, a distal end 99B of the push rod rests against the most proximal T-fastener 20C of the three T-fasteners 20A-20C that are lined up end-to-end near the distal tip 18B of the needle 18. Thus, it is seen that distal movement of the push rod by action of the ejector 50 of the ejection assembly 30 will cause the T-fasteners 20B and 20C to push the most distal T-fastener 20A out the needle distal tip 18B. FIG. 5 further shows the main spring 100 disposed in the spring cavity 68 about a portion of the actuator body 80 so as to urge the button 82 proximally outward.

FIG. 6B shows that in one optional embodiment the more proximal T-fasteners, such as the T-fastener 20B, can be configured to enable the suture(s) of a more distally positioned T-fastener, such as the T-fastener 20A, to pass by the more proximal T-fastener within the conduit of the needle 18. This is done in FIG. 6B by providing an indentation 102 in the body of the T-fastener 20B such that the suture 22A of the more distal T-fastener 20A can easily pass the T-fastener 20B. It is appreciated that more than one indentation can be included on one or more of the T-fasteners to enable multiple sutures to pass by. The sizes and shapes of the indentations can also vary from what is shown and described herein.

FIG. 6C shows that in another optional embodiment one or more of the T-fasteners, such as the T-fastener 20B, can be hollow and include a longitudinal slit so as to define a C-shaped cross section. The corresponding suture 22B can be affixed to an inner portion of the hollow T-fastener interior. The T-fastener 20B can be sized so as to exert a friction force against the inner surface of the needle 18. This serves to prevent unintended, premature ejection of the T-fastener before it is ejected at least indirectly by the push rod 99 or other component. When ejection is desired, the distal force of the push rod 99 is sufficient to overcome the friction force exerted by the T-fastener 20B against the inner surface of the needle 18 and eject the T-fastener.

Figure 7A:
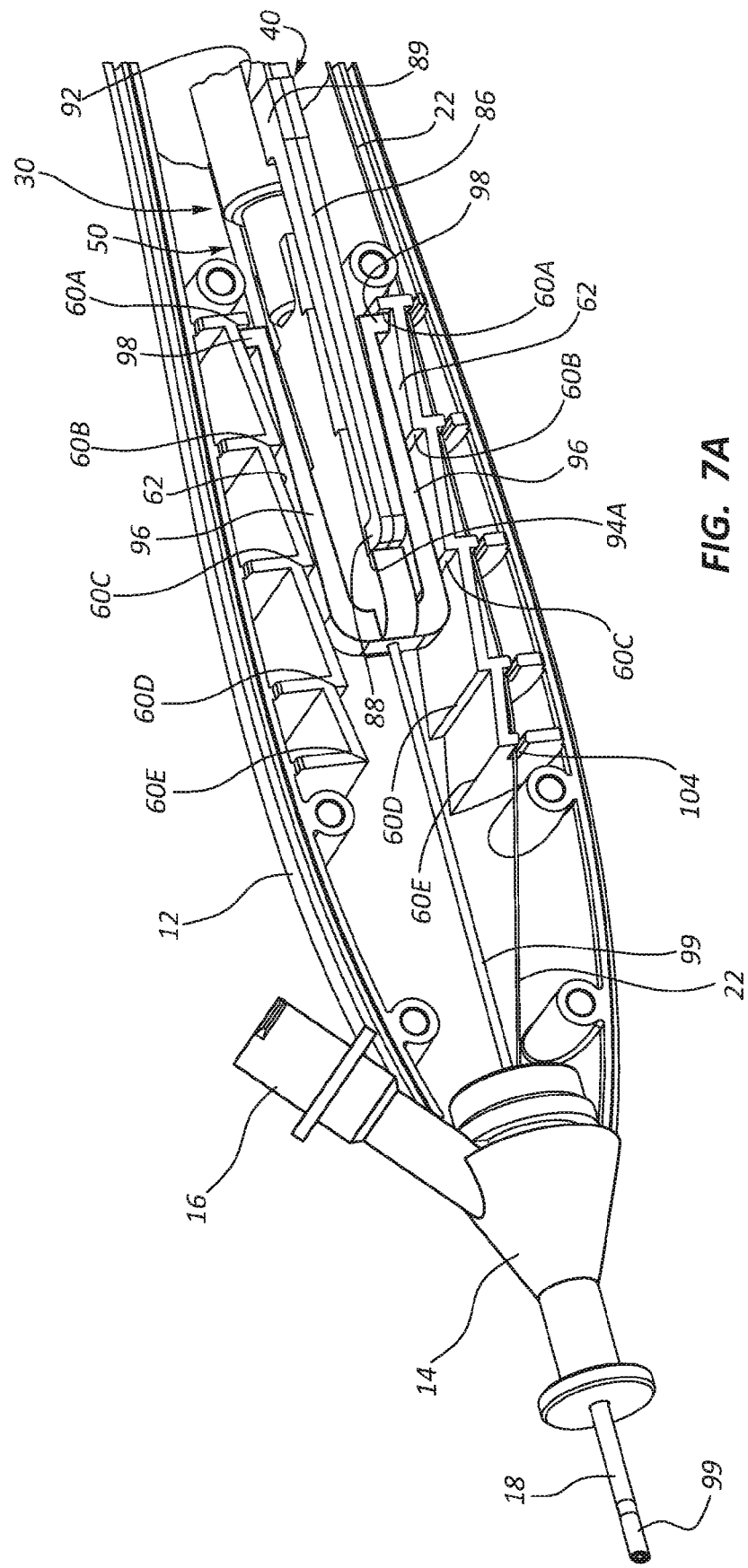

FIGS. 7A-7C describe operation of the device 10 according to one embodiment. In particular, FIG. 7A shows the device 10 cross-sectionally in an initial state, wherein the actuator 40 of the ejection assembly 30 is in an initial position before being actuated by a user via the pressing in of the button 82. Note that the feet 88 of the actuator arms 86 are disposed in the pockets 94A of the inclined teeth 95 of the ejector 50. In turn, the feet 98 of the ejector arms 96 are each disposed in the pockets 60A of the inclined teeth 62 of the housing 12. The distal end 99B of the push rod 99 is disposed adjacent the T-fasteners 20 in the needle 18, as shown in FIG. 6A. Note that FIG. 7A further shows a plurality of notches 104 defined in the supporting structure of the bottom set of inclined teeth 62 of the housing 12 that enable the sutures 22 proximally extending from the needle 18 to pass through the region of the housing in which the ejection assembly 30 is disposed, and out through a port in the housing (see also FIG. 1B). As seen in FIG. 2, in one embodiment a septum 72 including silicone or other suitable material can be disposed proximate the suture port defined in the proximal or other portion of the housing. The septum 72 can serve as a friction element for securing the sutures 22 passing therethrough so as to prevent the T-fasteners that are attached to the sutures from prematurely exiting the needle 18 before intended deployment.

FIG. 7B shows the state of the device 10 after the actuator button 82 has been pressed by a user. As shown, the actuator 40 moves distally, which in turn causes the ejector 50 to move distally by virtue of the engagement of the actuator arm feet 88 with the pockets 94A of the ejector inclined teeth 95. This distal movement of the ejector 50 causes the feet 98 of the ejector arms 96 to advance along the inclined teeth 62 of the housing from the pockets 60A to the pockets 60B. Seating of the ejector arm teeth 98 in the pockets 62B prevents subsequent proximal movement of the ejector.

Figure 8:
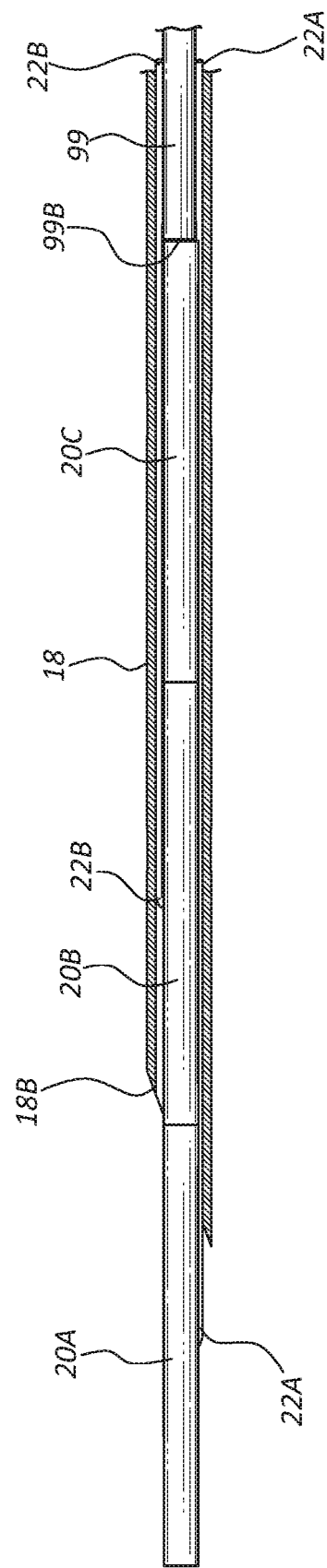
FIG. 8 is a cross sectional side view of the needle of the T-fastener suture delivery device of FIGS. 1A-1C, showing ejection of a first one of the T-fasteners.

The above distal movement of the ejector 50 causes the push rod 99 to advance distally within the needle 18. The amount of advancement of the ejector 50 and push rod 99 is configured so as to be sufficient to eject the most distally placed T-fastener 20A from the distal end 18B of the needle 18, as seen in FIG. 8. In this way, the T-fastener 20A can be delivered into the body of the patient in order to secure the stomach to the abdominal wall.

In particular, during operation of the device 10 the needle 18 is percutaneously inserted into the abdomen (or other suitable body portion) of the patient until the distal tip 18B of the needle is disposed within the stomach. Sampling via the injection port 16 as described further above can confirm proper needle distal tip placement. The actuation button 82 can then be pressed by a user, as shown in FIG. 7B, so that the first T-fastener 20A is ejected from the distal tip 18B of the needle 18 as shown in FIG. 8 and as described immediately above. This releases the T-fastener 20A into the interior of the stomach, at which point the T-fastener will move such that its length is substantially perpendicular to the suture 22A attached thereto. The needle 18 can then be withdrawn from the stomach and the suture 22A pulled distally out of the needle. The suture 22A, now extending through the percutaneous hole formerly occupied by the needle 18, can be cinched and secured with an external bolster, thus bringing the stomach wall into close proximity with the inner abdominal wall.

FIG. 7C shows that when the actuation button 82 is released after ejection of the T-fastener 20A from the needle 18, the actuator arm feet 88 slide proximally over the inclined teeth 95 to move from the pockets 94A to the pockets 94B, in preparation for ejection of the next T-fastener 20. The actuator 40 thus operates in a back-and-forth, ratcheting type of linear movement in incrementally moving the ejector 50 distally in a step-wise fashion.

The above T-fastener placement process can be repeated to insert additional T-fastener sutures into the patient without reloading the device 10 with T-fastener sutures. Specifically, with the ejection assembly in the configuration shown in FIG. 7C, i.e., the actuator arm feet 88 engaged with the ejector pockets 94B, and with the needle 18 of the device percutaneously inserted into a new location of the patient's body, the actuation button 82 is again pressed. This causes the actuator 40 to move distally within the housing 12 and, as before, move the ejector 50 distally as well, as shown in FIG. 9A. This distal movement of the ejector 50 causes the feet 98 of the ejector arms 96 to advance along the inclined teeth 62 of the housing 12 from the pockets 60B to the pockets 60C, which prevents subsequent proximal movement of the ejector.

The above distal movement of the ejector 50 causes the push rod 99 to advance further distally within the needle 18 a sufficient amount to eject the T-fastener 20B from the distal end 18B of the needle, as seen in FIG. 9A. In this way, the T-fastener 20A can be delivered into the body of the patient in order to further secure the stomach to the abdominal wall, as already described. FIG. 9B shows that when the actuation button 82 is released after ejection of the T-fastener 20B from the needle 18, the actuator arm feet 88 slide proximally over the inclined teeth 95 to move from the pockets 94B to the pockets 94C, in preparation for ejection of the next T-fastener 20.

Figure 10:
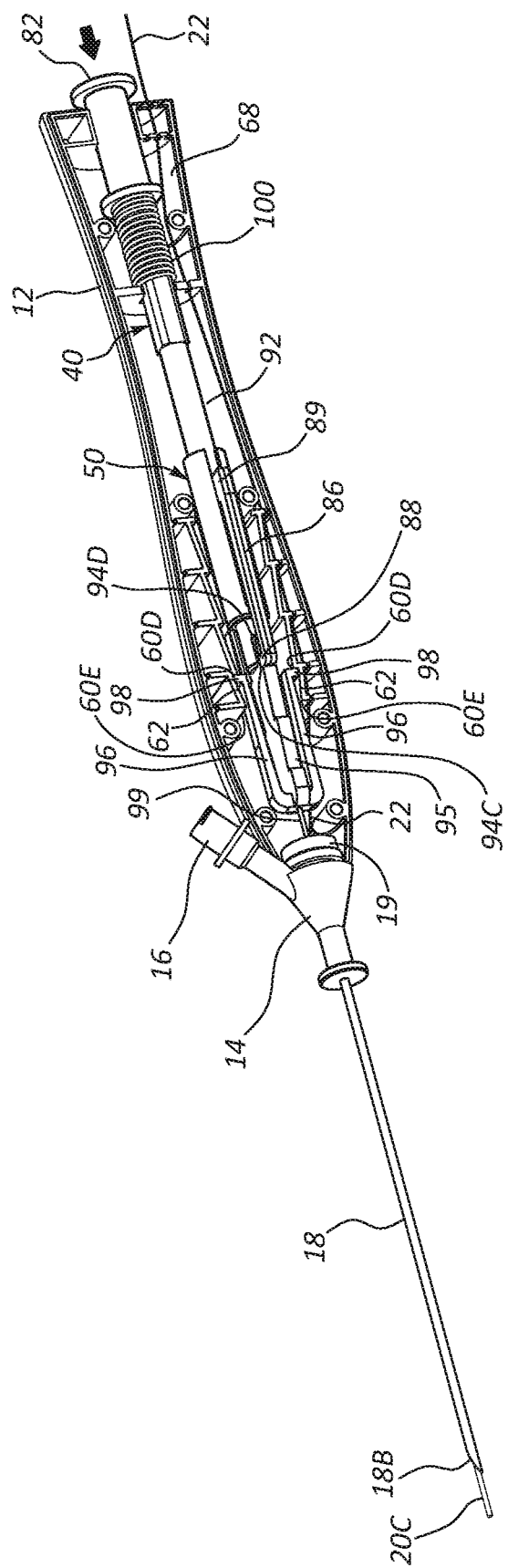
FIG. 10 is a cross-sectional perspective view of the T-fastener suture delivery device of FIGS. 1A-1C, showing operation thereof according to one embodiment.

FIG. 10 shows details regarding actuation of the ejection assembly 30 to eject the pre-loaded third T-fastener 20C. Specifically, with the ejection assembly in the configuration shown in FIG. 9B, i.e., the actuator arm feet 88 engaged with the ejector pockets 94C, the actuation button 82 is again pressed, which causes the actuator 40 to move distally within the housing 12 and, as before, move the ejector 50 distally as well, as shown in FIG. 10. This distal movement of the ejector 50 causes the feet 98 of the ejector arms 96 to advance along the inclined teeth 62 of the housing 12 from the pockets 60C to the pockets 60D, which prevents subsequent proximal movement of the ejector.

Figure 11A:
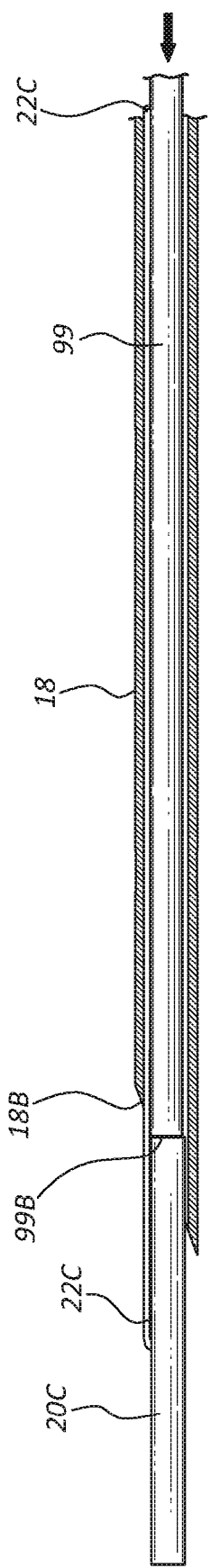
FIGS. 11A and 11B are cross sectional side views of the needle of the T-fastener suture delivery device of FIGS. 1A-1C, showing ejection of a last one of the T-fasteners and blunting of the needle tip by a push rod, according to one embodiment.

The above distal movement of ejector 50 causes the push rod 99 to advance further distally within the needle 18 a sufficient amount to eject the third T-fastener 20C from the distal end 18B of the needle, as seen in FIGS. 10 and 11A. In this way, the T-fastener 20C can be delivered into the body of the patient in order to further secure the stomach to the abdominal wall, as already described. When the actuation button 82 is released after ejection of the third T-fastener 20C from the needle 18, the actuator arm feet 88 slide proximally over the inclined teeth 95 to move from the pockets 94C to the pockets 94D.

Once the three T-fasteners 20A-20C have been deployed one-by-one in step-wise fashion as just described, the actuation button 82 can be pressed again, which causes the actuator 40 to move distally within the housing 12 and again move the ejector 50 distally. This distal movement of the ejector 50 causes the feet 98 of the ejector arms 96 to advance along the inclined teeth 62 of the housing 12 from the pockets 60D to the pockets 60E, which prevents subsequent proximal movement of the ejector.

Figure 11B:
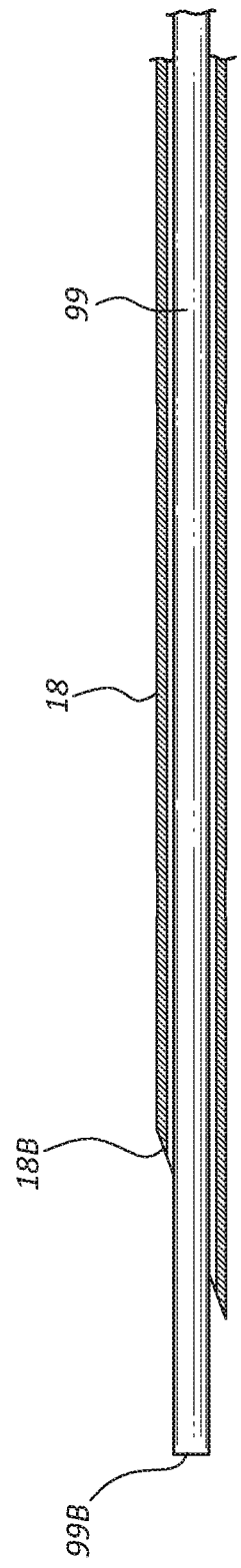

The above distal movement of ejector 50 causes the push rod 99 to advance further distally within the needle 18 such that the distal end 99B thereof extends past the distal end 18B of the needle, as seen in FIG. 11B. This enables the push rod 99 to serve as a blunting member for the distal tip 18B of the needle 18 in order to prevent unintended sticks therewith. When the actuation button 82 is released after extension of the push rod distal end 99B past the needle distal tip 18B, the actuator arm feet 88 slide proximally away from the pockets 94D, and thus no further distal movement of the ejector 50 by the actuator can occur. It is appreciated that the device 10 and the above process can be configured to deploy any suitable number of T-fasteners preloaded in the device.

Figure 12:
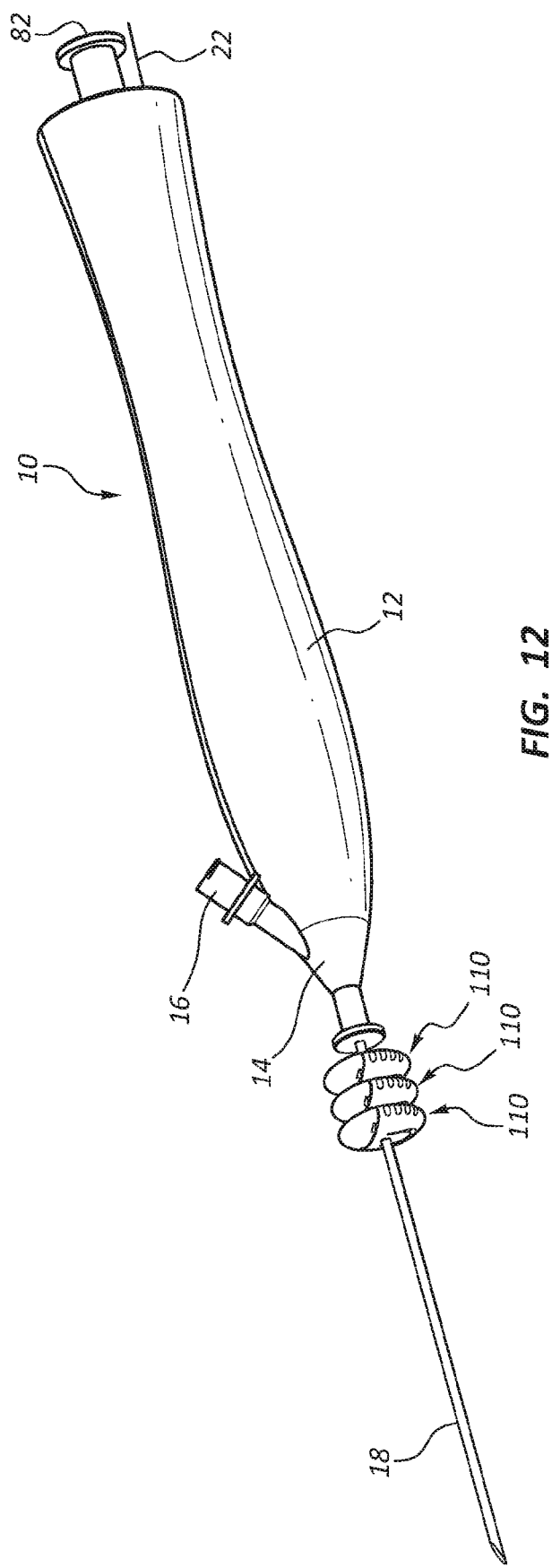
FIG. 12 is a perspective view of a T-fastener delivery device including a plurality of external bolsters, according to one embodiment.

FIG. 12 shows that in one embodiment a plurality of external bolsters 110 can be included with the device 10 so as to enable external securement of the T-fastener sutures after deployment by the device. As shown, the bolsters 110 are pre-disposed on the needle 18 of the device 10 and are configured to distally slide off the needle and on to the suture 22 to cinch up against the patient's skin after the T-fastener 20 has been inserted and secured within the stomach. In the present embodiment, one bolster 110 is included for each T-fastener 20 to be deployed by the device 10.

FIGS. 13A and 13B show various details of the bolsters 110 according to present embodiment. As shown, the bolster 110 includes a bolster housing 112 that is rotatably mated to a twist portion 122. The bolster housing 112 defines a cavity 114 in communication with a central hole 116 through which the needle 18/suture 22 extends. A tab 118 is included on the bolster housing 112 for securing the twist portion 122 thereto when the two parts are mated. A nub 120 extends from the interfacing face of the bolster housing 112 for limiting movement of the twist portion 122.

The twist portion 122 of the bolster 110 includes a post 124 sized to be received within the cavity 114 of the bolster housing 112. A post hole 126 is defined through the post 124 so as to be co-linear with the central hole 116 of the bolster housing 112 when the two holes are aligned. An engagement feature 130 is included on the terminal end of the post 124 to engage with the tab 118, which in turn enables the twist portion to matingly and rotatably engage with the bolster portion. Two recesses 128A and 128B are included on an interfacing face of the twist portion 122 and are sized to selectively engage the nub 120 in a releasable friction fit when the twist portion is manually manipulated.

FIGS. 14A and 14B show the manner of engagement between the engagement feature 130 and the tab 118 to enable rotational mating of the bolster housing 112 and the twist portion post 124. FIGS. 14A and 14B further show the manner of use of the bolster 110. Specifically, after one of the T-fasteners 20 has been placed within the stomach and the suture 22 connected thereto extends from the percutaneous hole made by the needle during the T-fastener placement, the bolster 110 is distally slid down the needle from its initial position (FIG. 12) until it slides past the needle distal tip 18B and over a portion of the suture before it has been separated from the device 10. Note that at this point the bolster housing 112 and the twist portion 122 are positioned with the nub frictionally received into the recess 128A such that the central hole 116 and the post hole 126 are aligned so that the suture can freely slide therethrough.

The bolster 110 can then be slid along the suture 22 until it is positioned snugly against the skin of the patient. The twist portion 122 can then be rotated approximately 180 degrees until the nub 120 is frictionally received in the recess 128B. This causes the suture 22 to bind between the central hole 116 and the post hole 126, thus securing the bolster 110 in place on the suture and ensuring that the corresponding T-fastener 20 remains snug against the inner stomach wall. The suture 22 can be removed from the device before final placement of the bolster 110 has been completed. The twist portion 122 is rotatable with respect to the bolster housing 112, if desired, to again free the suture 22.

Figure 15B:
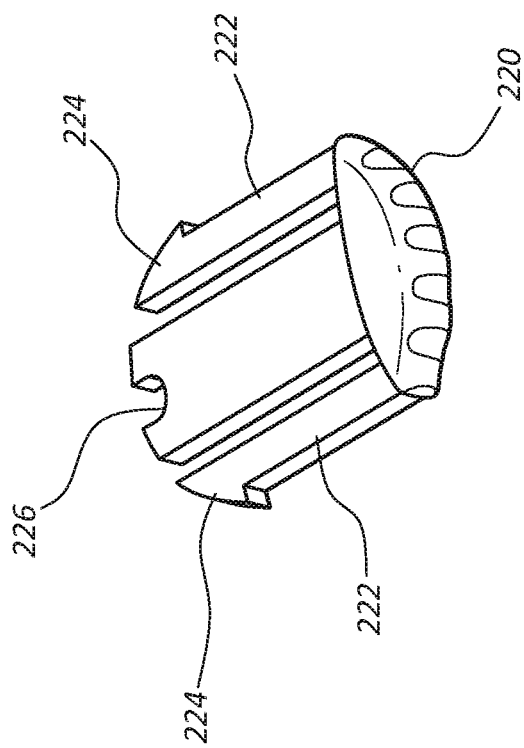
FIGS. 15A and 15B are perspective views of components of an external bolster according to one embodiment.
Figure 15A:
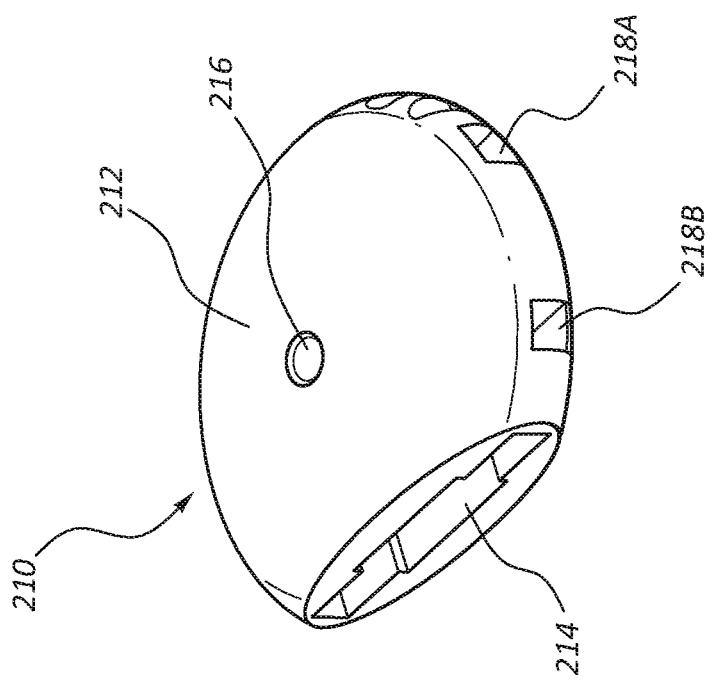

FIGS. 15A-16D depict details of a bolster 210 that can be used in securing sutures 22 used with the device 10 according to another embodiment. As shown in FIGS. 15A and 15B, the bolster 210 includes a bolster housing 212 and a slider portion 220. The bolster housing 212 defines a cavity 214 and a central hole 216. A first slot pair 218A and a second slot pair 218B are also included on the bolster housing 212.

The slider portion 220 includes a pair of slider arms 222 extending parallel to one another and each including on a terminal end thereof an engagement tooth 224. A suture notch 226 is also included on the slider portion 220.

FIGS. 16A-16D show the manner of operation of the bolster 210. After the T-fastener 20 has been placed in the stomach, the bolster 210 is slid off the needle 18 and down the suture 22 until the bolster is cinched against the skin of the patient. Note that in the open configuration of the bolster 210 in FIG. 16A, the slider portion 220 is disposed in the cavity 214 of the bolster housing 212 such that the engagement teeth 224 of the slider portion are disposed in the first pair of slots 218A to prevent unintended separation of the two portions of the bolster (see also FIG. 16C).

Figure 16A:
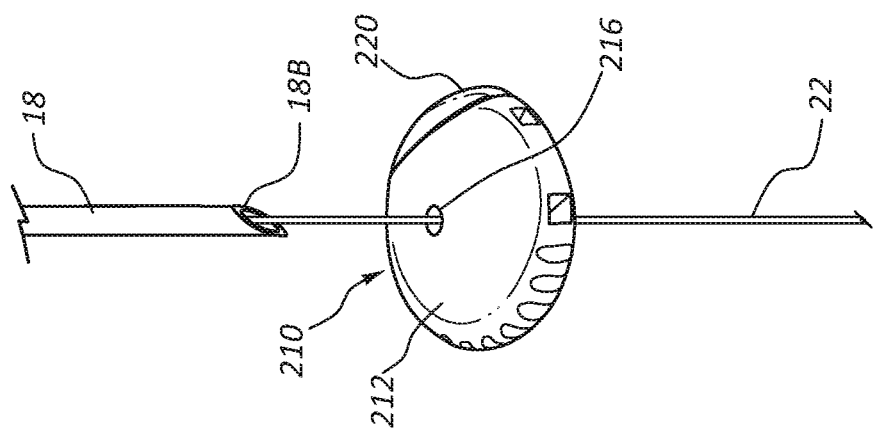
Figure 16B:
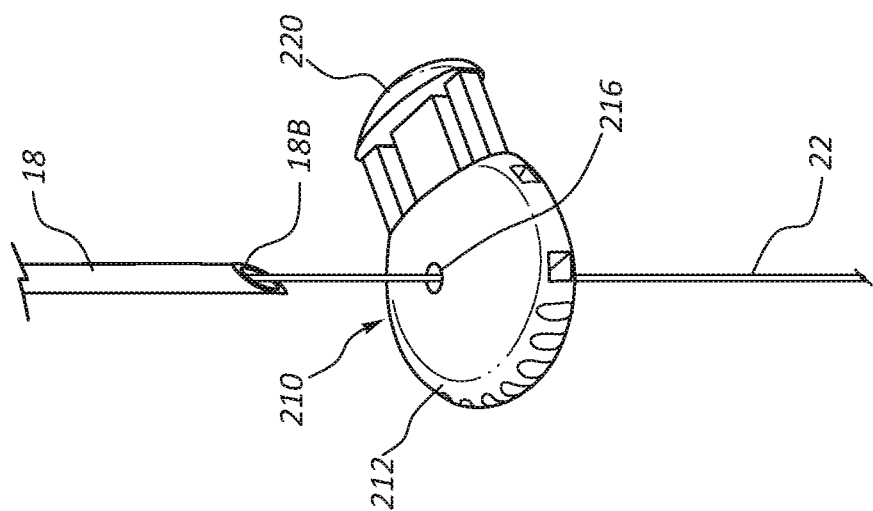

Once in position, the slider portion 220 is manually pushed further into the bolster housing cavity 214 such that the engagement teeth 224 move from the first pair of slots 218A to the second pair of slots 218B, which locks the slider portion in the closed configuration shown in FIG. 16B. Note that resilient deformation of the slider arms 222 enables the movement of the engagement teeth 224 between the two pairs of slots 218A, 218B. As seen in FIGS. 16C and 16D, the full insertion of the slider portion 220 into the bolster housing cavity 214 captures the suture 22 between the slider portion and the bolster housing 212 and prevents relative movement between the bolster 210 and the suture. Note that the suture notch 226 helps facilitate passage of the suture between the two components. It is appreciated that in addition to the designs depicted and discussed herein, other bolster designs can be employed with the device 10. In yet another embodiment, no bolster is included or pre-loaded with the device.

Figure 17:
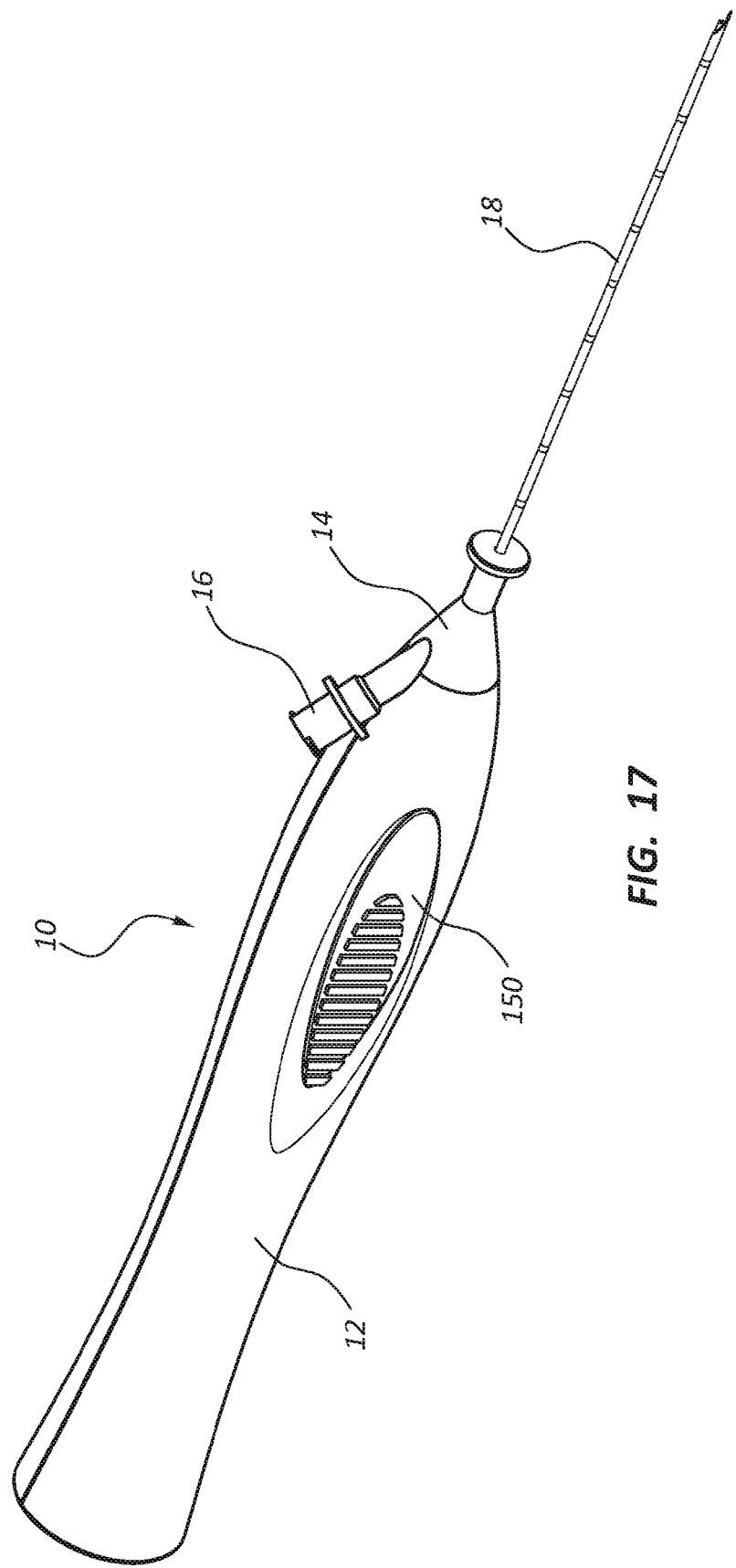
FIG. 17 is a perspective view of a T-fastener-equipped suture delivery device according to one embodiment.

FIG. 17 shows that in one embodiment slide button 150 and associated components can be included with the device 10, either in addition to (as here) or in place of the actuation button 82 shown in FIGS. 7A-10 in order to selectively move the ejection assembly 30. As such, the slide button 150 can be manually slid distally and proximally to actuate the actuator 40 in a manner similar to that achieved by pressing the actuation button 82 in previous embodiments.

Figure 18B:
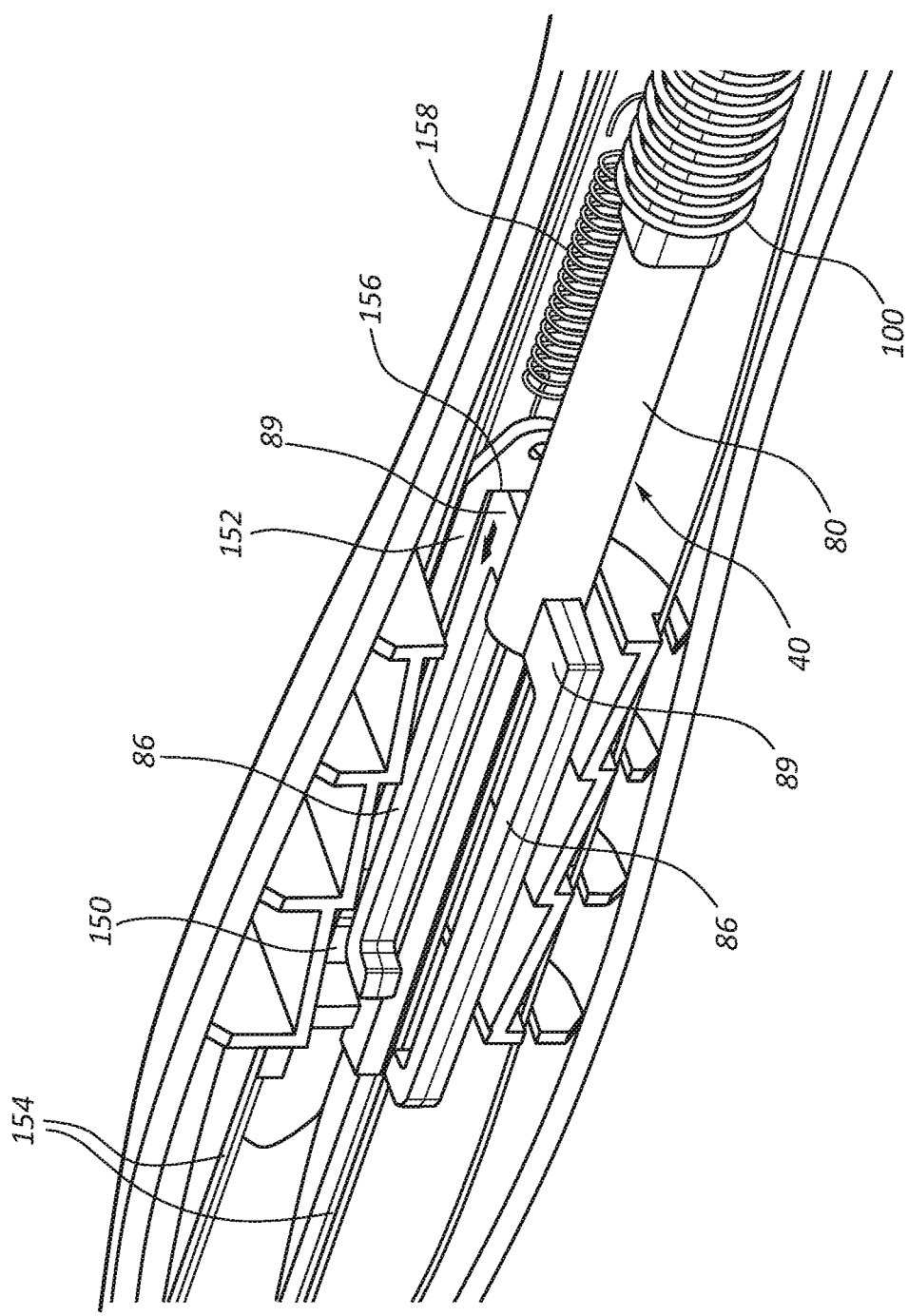

FIGS. 18A and 18B depict details regarding the structure enabling use of the slide button 150 to move the actuator 40. In particular, the slide button 150 is attached to a slider bar 152, which in turn is slidably disposed on a pair of rails 154 defined by the housing 12. The slider bar 152 includes a push surface near the proximal end thereof. Also, a slider bar spring 158 is attached to the slider bar 152 to urge its return to a proximal position within the housing 12 after the slide button is slid distally by a user.

FIG. 18B shows the manner of engagement of the slider bar 152 with the actuator 40, wherein the slider bar is disposed within the housing such that the push surface 156 of the slider bar is disposed adjacent to one of the shoulders 89 of the actuator arms 86. In this configuration, distal sliding movement of the slide button 150 as shown in FIG. 17 causes the slider bar 152 to contact and distally push the actuator 40 by virtue of the engagement of the slider bar push surface 156 with the actuator arm shoulder 89. This enables the actuator 40 to operate in the same fashion as was described in connection with FIGS. 7A-10 when the actuation button 82 at the proximal end of the device 10 was used to distally move the actuator. The slider bar spring 158 assists in returning the slider bar 152 and attached slide button 150 to an initial position. It is therefore appreciated that one or more configurations may be employed to eject the T-fasteners from the device 10 one-by-one, in succession without the need for reloading the device, thus enabling suture placement to proceed simply and relatively quickly.

In addition to gastropexy, it is also appreciated that the device disclosed herein can be employed to deploy sutures in a variety of other applications. Though step-wise incremental ejection of the T-fasteners has been discussed herein, it is appreciated that in one embodiment the T-fasteners can be ejected from the needle in a continuous fashion, or with continuous or smooth push rod movement. Moreover, it is appreciated that the ejection assembly can take many forms including, in one embodiment, a simple assembly for enabling the user to manually actuate a relatively direct distal pushing motion to the push rod so as to eject the T-fasteners from the needle, similar to a syringe (housing) and plunger (push rod) arrangement. In such a case, a series of nubs and detents could be disposed between the housing and the plunger to preferentially advance the plunger incrementally in ejecting the T-fasteners. In yet another embodiment, the assembly could include a rotational arrangement wherein a plunger or other device is rotated relative the housing in order to cause distal advancement of a push rod or other component in order to eject the T-fasteners.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A delivery device, comprising:
   a housing including a plurality of teeth defining a plurality of pockets on an interior side surface;
   a needle extending from a distal end of the housing;
   a plurality of T-fasteners, each of the T-fasteners including:
      a fastener portion disposed in a lumen of the needle; and
      a suture portion extending toward a proximal end of the housing; and
   an ejection assembly including:
      an actuator designed for reciprocal movement between a first position and a second position, wherein the fastener portion is ejected from a distal end of the needle in the second position; and
      an ejector designed for incremental distal movement, the ejector including:
         a plurality of teeth designed to engage the actuator; and
         an ejector arm designed to engage the plurality of pockets.

2. The delivery device according to claim 1, wherein the plurality of T-fasteners includes three fastener portions disposed in the lumen of the needle.

3. The delivery device according to claim 1, wherein the plurality of teeth defining the plurality of pockets comprises:
   a first plurality of teeth and pockets positioned on a first interior side surface; and
   a second plurality of teeth and pockets positioned on a second interior side surface opposite of the first interior side surface.

4. The delivery device according to claim 3, wherein the ejector arm is designed to engage the first plurality of teeth and pockets, and wherein the ejector further comprises a second arm designed to engage the second plurality of teeth and pockets.

5. The delivery device according to claim 4, wherein the plurality of teeth of the ejector comprises a first plurality of teeth and a second plurality of teeth opposite of the first plurality of teeth.

6. The delivery device according to claim 5, wherein the actuator comprises a first member designed to engage the first plurality of teeth and a second member designed to engage the second plurality of teeth upon movement of the actuator from the first position to the second position.

7. The delivery device according to claim 1, wherein the ejection assembly further includes a push rod extending distally from the ejector, the push rod contacting the fastener portion of each of the plurality of T-fasteners in succession upon movement of the actuator from the first position to the second position.

8. The delivery device according to claim 1, further comprising a plurality of external bolsters disposed on the needle, wherein each of the plurality of external bolsters is designed to slide from the needle and onto the suture portion of each of the plurality of T-fasteners in the second position to secure each of the plurality of T-fasteners to a patient.

9. The delivery device according to claim 1, wherein at least one of the plurality of T-fasteners includes an indentation for passage of the suture portion of one or more T-fasteners.

10. The delivery device according to claim 1, wherein at least one of the T-fasteners is a hollow T-fastener that defines a C-shaped cross-sectional configuration, the hollow T-fastener designed to impose a friction force against an inner surface of the needle.

11. The delivery device according to claim 1, further comprising a needle hub attached to the housing, the needle hub including a lumen in fluid communication with the needle lumen, wherein a valve is disposed in a proximal end of the needle hub lumen to prevent fluids from entering the housing.

12. The delivery device according to claim 11, wherein the needle hub further comprises an injection port, the injection port including a lumen in fluid communication with the lumen of the needle.

13. The delivery device according to claim 1, wherein the actuator is biased in the first position by a spring disposed in the housing.

* * * * *